(12) United States Patent
Fram

(10) Patent No.: US 9,323,402 B1
(45) Date of Patent: Apr. 26, 2016

(54) IMAGE NAVIGATION

(75) Inventor: Evan K. Fram, Paradise Valley, AZ (US)

(73) Assignee: D.R. Systems, Inc., San Diego, CA (US)

(*) Notice: Subject to any disclaimer, the term of this patent is extended or adjusted under 35 U.S.C. 154(b) by 608 days.

(21) Appl. No.: 13/479,558

(22) Filed: May 24, 2012

Related U.S. Application Data

(60) Provisional application No. 61/490,534, filed on May 26, 2011.

(51) Int. Cl.
| | |
|---|---|
| *G06F 3/041* | (2006.01) |
| *G06F 3/044* | (2006.01) |
| *G06F 3/023* | (2006.01) |
| *G06F 3/0482* | (2013.01) |
| *G06F 3/0485* | (2013.01) |
| *G06F 3/0488* | (2013.01) |
| *G06T 11/20* | (2006.01) |

(52) U.S. Cl.
CPC .............. *G06F 3/044* (2013.01); *G06F 3/0236* (2013.01); *G06F 3/0482* (2013.01); *G06F 3/0485* (2013.01); *G06F 3/04886* (2013.01); *G06T 11/206* (2013.01)

(58) Field of Classification Search
CPC ..... G06F 3/044; G06F 3/0482; G06F 3/0485; G06T 11/206
USPC .................................................. 345/173–174
See application file for complete search history.

(56) References Cited

U.S. PATENT DOCUMENTS

| | | |
|---|---|---|
| 8,954,884 B1 | 2/2015 | Barger |
| 2003/0055686 A1 | 3/2003 | Satoh |
| 2004/0249303 A1* | 12/2004 | Serra .............................. 600/545 |
| 2005/0114788 A1 | 5/2005 | Fabritius |
| 2006/0017692 A1 | 1/2006 | Wehrenberg |
| 2008/0094368 A1 | 4/2008 | Ording |
| 2009/0035218 A1* | 2/2009 | Ross ...................... A61B 5/415 424/9.1 |
| 2009/0138800 A1 | 5/2009 | Anderson |
| 2010/0131294 A1 | 5/2010 | Venon |
| 2010/0245360 A1* | 9/2010 | Song et al. .................... 345/441 |
| 2010/0293500 A1* | 11/2010 | Cragun et al. ................ 715/784 |
| 2011/0214050 A1* | 9/2011 | Stambaugh ......... G06F 3/04817 715/234 |
| 2011/0249002 A1* | 10/2011 | Duplessis et al. ............. 345/440 |
| 2011/0252320 A1* | 10/2011 | Arrasvuori ............ G06F 1/1626 715/704 |
| 2012/0036466 A1* | 2/2012 | Venon et al. ................... 715/772 |
| 2012/0051609 A1* | 3/2012 | Avinash et al. ............... 382/128 |
| 2012/0133601 A1 | 5/2012 | Marshall |
| 2012/0253845 A1 | 10/2012 | Bocirnea |
| 2013/0141366 A1 | 6/2013 | Ritter |

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

(Continued)

*Primary Examiner* — Temesgh Ghebretinsae
*Assistant Examiner* — Kwin Xie
(74) *Attorney, Agent, or Firm* — Knobbe, Martens, Olson & Bear LLP

(57) ABSTRACT

Systems and methods for navigating between images of multiple exams using gestures performed on a touch sensitive input device.

29 Claims, 30 Drawing Sheets

(56) References Cited

OTHER PUBLICATIONS

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions. Accessed on Feb. 9, 2015.

AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%20interWORKS%20RISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 Brit Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.

DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.

FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.

FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.

GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.

Handylife.com—Overview of Handy Patients Enterprise, in 2 page printout. Accessed from http://www.handylife.com/en/software/overview.html. Accessed on Feb. 18, 2015.

Handylife.com—Features of Handy Patients Enterprise, in 4 page printout. Accessed from http://www.handylife.com/en/software/features.html. Accessed on Feb. 18, 2015.

Handylife.com—Screenshots of Handy Patients Enterprise, in 2 page printout. Accessed from http://www.handylife.com/en/software/screenshots.html. Accessed on Feb. 18, 2015.

iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.

imageanalysis, dynamika, 2 page color brochure. Downloaded from http://www.imageanalysis.org.uk/what-we-do. Accessed on Feb. 9, 2015.

imageanalysis, MRI Software, in 5 page printout. Accessed at http://www.imageanalysis.org.uk/mri-software. Accessed on Feb. 9, 2015.

IMSI, Integrated Modular Systems, Inc., Hosted / Cloud PACS in one page printout. Accessed at http://www.imsimed.com/#!products-services/ctnu. Accessed on Feb. 9, 2015.

Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.

Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.

Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.

Intuitive Imaging Informatics, ImageQube, 1 page in color. Downloaded from http:www.intuitiveimaging.com/2013/pdf/ImageQube%20one-sheet.pdf. Accessed on Feb. 9, 2015.

Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.

LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.

LUMEDX Cardiovascular Information System, CardioPACS, one page in color printout. Accessed at http://www.lumedx..com/pacs.aspx. Accessed on Feb. 9, 2015.

McKesson Enterprise Medical Imaging and PACS | McKesson, 1 page (color) printout. Accessed at http://www.mckesson.com/providers/health-systems/diagnostic-imaging/enterprise-medical-imaging. Accessed on Feb. 9, 2015.

Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.

Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.

NOVARAD Enterprise Imaging Solutions, NOVAPACS, 2 page (color) printout. Accessed at http://ww1.novarad.net/novapacs. Accessed on Feb. 9, 2015.

(56) References Cited

OTHER PUBLICATIONS

PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.phillips.com/main/products/heathcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.

\* cited by examiner

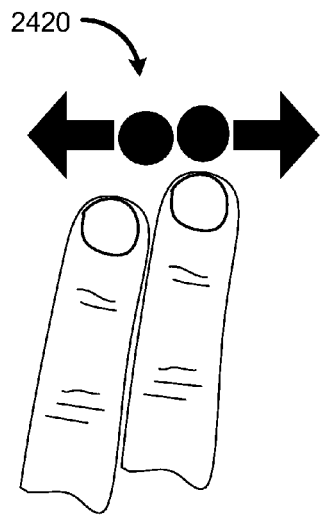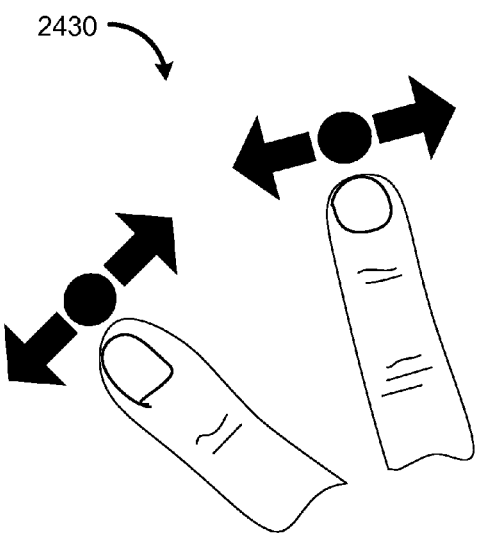
Next car in price category　　　Fig. 24　　Increase or decrease price category

IMAGE NAVIGATION

CROSS-REFERENCE TO RELATED APPLICATIONS

This application claims the benefit of priority under 35 U.S.C. §119(e) of U.S. Provisional Application No. 61/490,534, filed May 26, 2011, the disclosure of which is hereby incorporated by reference in its entirety.

BACKGROUND

The volume of digitally accessible information continues to grow rapidly. At the same time, the screen size of computing devices continues to shrink with the widespread adoption of handheld computing devices such as smartphones and tablets. There is a need for better ways of presenting and interacting with information that accommodates these trends.

SUMMARY

In one embodiment, a method of navigating between images of multiple image series, wherein each image series comprises multiple images, comprises displaying, on a display of a computing device having one or more computer processors, a first image of a first series of images of a first series type within a first exam of a patient. The method further comprises, in response to receiving a first input from a user of the computing device, selecting, by the computing device, another image in the first series of images and, in response to receiving a second input from the user of the computing device, selecting, by the computing device, another image from a second series of images of the first series type within a second exam of the patient, wherein the selected another image within the second exam is selected to match an anatomic position of the first image. The method further comprises displaying the selected another image on the display of the computing device.

In one embodiment, a computing system comprises one or more computer processors configured to execute software instructions, a touch sensitive input device configured to detect user interactions with the touch sensitive input device, and a tangible computer readable medium. The tangible computer readable medium may store a data structure indicating relationships between image series of respective exams, each of the exams including a plurality of image series each including a plurality of images, software code configured for execution by the one or more computer processors in order to cause the computing system to perform operations including: in response to a first user interaction, selecting an image for display that is in a same exam and having a same series type as a currently displayed image, in response to a second user interaction, selecting an image of a second image series of a second exam, wherein the software code is configured to cause the computing system to automatically select a second image series of the second exam based on a relationship in the data structure between a first series type of the first exam and a second series type of the second exam. The operations may further comprise displaying the selected image on the display.

In one embodiment, a method of navigating between images of multiple image series, wherein each image series comprises multiple images, comprises displaying, on a display of a computing device having one or more computer processors, a first image of a first series of images of a first series type, in response to receiving a first input from a user of the computing device, selecting, by the computing device, another image in the first series of images, and in response to receiving a second input from the user of the computing device, selecting, by the computing device, another image from a second series of images, wherein the selected another image is selected to substantially match an anatomic position of the first image. The method may further comprise displaying the selected another image on the display of the computing device.

In one embodiment, a method of navigating between data items of multiple data sets, wherein each data set comprises multiple data items, comprises displaying, on a display of a computing device having one or more computer processors, a first data item of a first data set, in response to receiving a first input from a user on a touch sensitive input device of the computing device, selecting, by the computing device, another data item in the first data set, and in response to receiving a second input from the user of the touch sensitive input device, selecting, by the computing device, a second data item of a second data set, wherein the second data item is selected to substantially match one or more attributes of the first data item. The method may further comprise displaying the second data item on the display of the computing device. In one embodiment, a first plurality of data sets including the first data set and the second data set are associated with a first collection of data sets. In one embodiment, the method further comprises, in response to receiving a third input from the user of the touch sensitive input device, selecting, by the computing device, a third data item of a third data set of a second collection of data sets, wherein the third data item is selected to substantially match one or more attributes of the first data item. In an embodiment applied to medical images, the data items may include medical images, the data sets may include image series, and the collections may include exams. In an embodiment applied to product configurations (e.g., automobile types, makes, models, etc.), the data items may include automobile profiles and/or images, the data sets may include vehicle configurations (e.g., sedan, convertible, full size), and the collections may include automobile manufacturers, model years, colors, or other attributes. The method may be applied to any other types of data items, data sets, and/or collections.

In one embodiment, a method of navigating between data items of multiple data sets, wherein each data set comprises multiple data items, comprises displaying, on a display of a computing device having one or more computer processors, a first data item of a first data set, in response to receiving input from the user, selecting, by the computing device, a second data item of a second data set, wherein the second data item is selected to substantially match one or more attributes of the first data item, and displaying the second data item on the display of the computing device.

BRIEF DESCRIPTION OF THE DRAWINGS

FIG. 19a depicts a computing device displaying images of a first group of series (e.g., as shown in FIG. 18a), while

FIG. 24 illustrates an example user interface that may be generated and updated using navigation techniques discussed with reference to FIG. 23, for example.

DETAILED DESCRIPTION

Figure 1A:
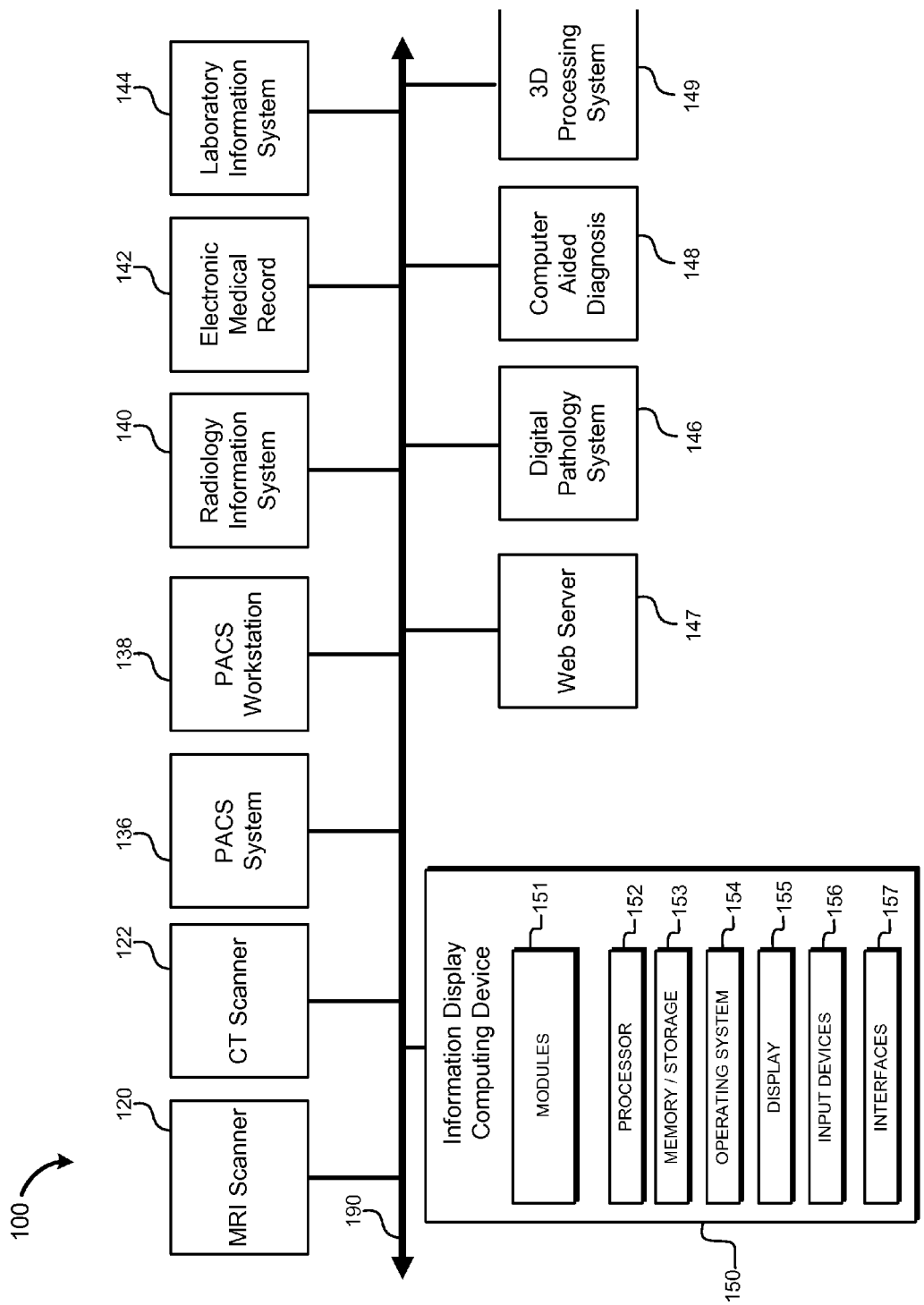
FIGS. 1a and 1b are system diagrams illustrating various components of systems for managing data utilizing certain systems and methods described herein.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. In some embodiments, a user (or viewer) is an individual that views any other type of information, such as product configuration information. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a tangible computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Introduction

Those that interface with medical data, such as doctors, want access to information anytime, anywhere, and on any device. Computing devices continue to shrink, but the volume of information doctors need to view is growing dramatically with adoption of electronic medical records (EMRs) and an increase in size of medical imaging exams. While handheld devices such as smartphones and tablets can be used to access and display medical images, current methods of interacting with large amounts of information on small devices are suboptimal. There is a need for systems and method for interacting with information that are more efficient and intuitive, both on handheld devices and larger computing systems such as PCs and computer workstations.

Systems and methods described herein are applicable to a wide range of uses. For purposes of illustration the following embodiments are described herein:

Medical imaging

Electronic Medical Records (EMR) systems

E-commerce

Interacting with N-dimensional data, with an illustration of 6-dimensional data

However the systems and methods described herein may be used in other areas, for example:

Navigation of information in a database or other data structure, e.g. car inventory As a way of providing input, e.g., customizing a product.

Systems and Methods described herein are flexible:

The various dimensions of information may be categorical or continuous.

Any type of information may be utilized, e.g. image, text, number, etc.

While the embodiments are illustrated with handheld devices, any computing device may be utilized including a computer workstation, PC, kiosk, medical scanner, etc.

While embodiments illustrate user input with a touchscreen and buttons, input could be provided by any input device, e.g., mouse, trackball, joystick, microphone, video device that detects movements of a user, etc.

Example Computing Systems

FIG. 1 is a system diagram illustrating various components of a system 100 for managing data utilizing certain systems and methods described herein. As shown, the system 100 may include an Information Display Computing Device 150 (or simply "computing device 150" or "device 150") and may include other systems, including those shown in FIG. 1.

The information display computing device 150 may take various forms. In one embodiment, the information display computing device 150 may be a computer workstation having modules 151, such as software, firmware, and/or hardware modules. In other embodiments, modules 151 may reside on another computing device, such as a web server, and the user directly interacts with a second computing device that is connected to the web server via a computer network. The modules 151 will be described in detail below.

Figure 2:
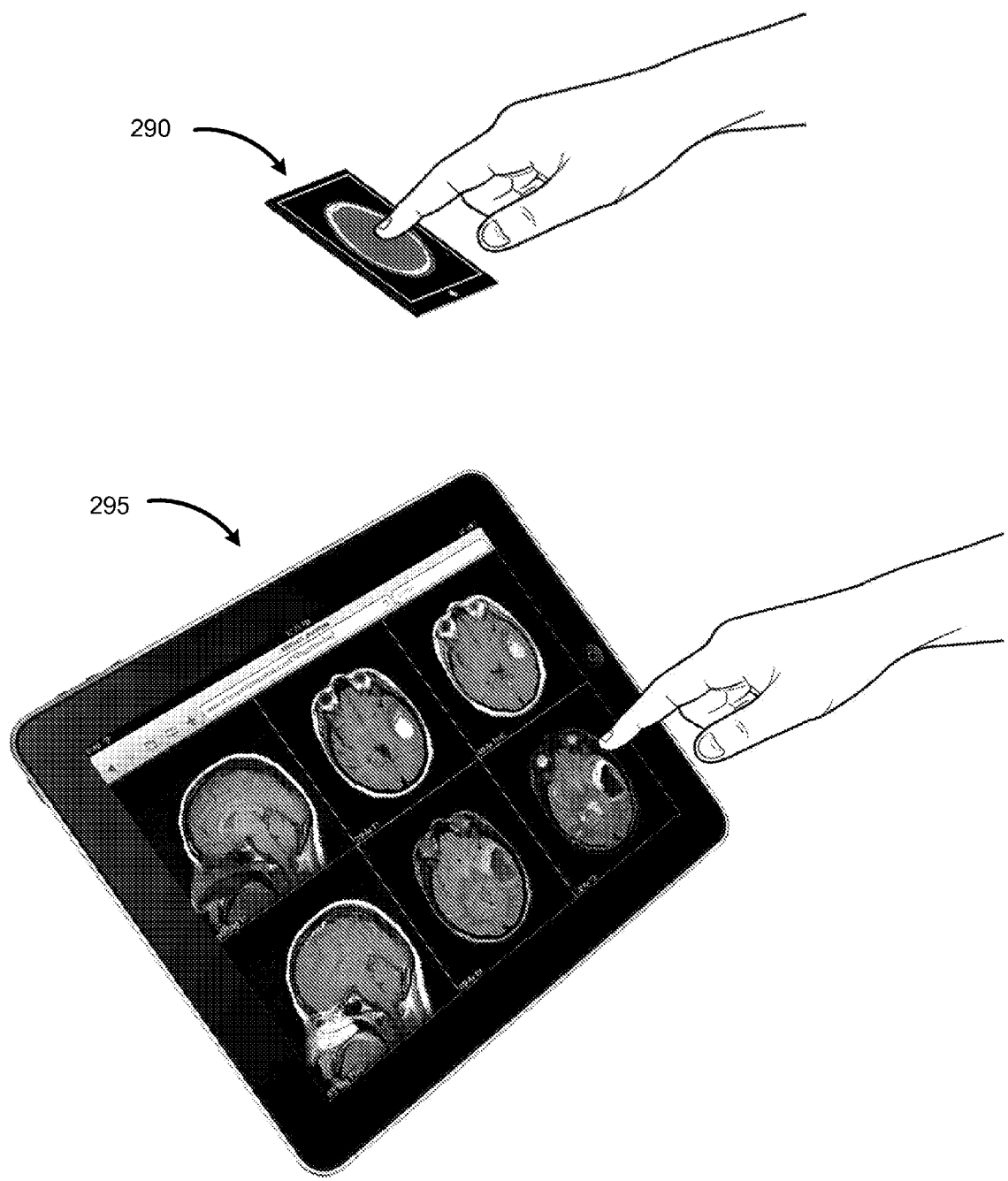
FIG. 2 illustrates two mobile information display computing devices.

In various embodiments, the information display computing device 150 comprises a server, a desktop computer, a workstation, a laptop computer, a mobile computer, a Smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example. In one embodiment, for example, the information display computing device 150 comprises a tablet computer, such as the tablet computer illustrated in FIG. 2. As illustrated in FIG. 2, a touchscreen of the tablet computer provides a user interface that is responsive to contact with a human hand/finger or stylus.

The information display computing device 150 may run an off-the-shelf operating system 154 such as a Windows, Linux, MacOS, Android, or iOS. The information display computing device 150 may also run a more specialized operating system which may be designed for the specific tasks performed by the computing device 150.

The information display computing device 150 may include one or more computing processors 152. The computer processors 152 may include central processing units (CPUs), and may further include dedicated processors such as graphics processor chips, or other specialized processors. The processors generally are used to execute computer instructions based on the information display modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The information display computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The information display computing device 150 may also include or be interfaced to one or more display devices 155 that provide information to the users. Display devices 155 may include a video display, such as one or more high-resolution computer monitors, or a display device integrated into or attached to a laptop computer, handheld computer, Smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The information display computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The information display computing device 150 may also include one or more interfaces 157 which allow information exchange between information display computing device 150 and other computers and input/output devices using systems such as Ethernet, Wi-Fi, Bluetooth, as well as other wired and wireless data communications techniques.

The modules of the information display computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of information display computing device 150 may be combined into fewer components and modules or further separated into additional components and modules.

The information display computing device 150 may communicate and/or interface with other systems and/or devices. In one or more embodiments, the computer device 150 may be connected to a computer network 190. The computer network 190 may take various forms. It may be a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanner 120. The MRI scanner 120 may be used to acquire MRI images from patients, and may share the acquired images with other devices on the network 190. One or more CT scanners 122 may be coupled to the network 190. The CT scanners 122 may also be used to acquire images and, like the MRI scanner 120, may then store those images and/or share those images with other devices via the network 190. Any other scanner or device capable of inputting or generating information that can be displayed as images or text could be included, including ultrasound, angiography, nuclear medicine, radiography, endoscopy, pathology, dermatology, etc.

Also connected to the network 190 may be a Picture Archiving and Communications System (PACS) 136 and PACS workstation 138. The PACS System 136 is typically used for the storage, retrieval, distribution and presentation of images (such as those created and/or generated by the MRI scanner 120 and CT Scanner 122). The medical images may be stored in an independent format, an open source format, or some other proprietary format. A common format for image storage in the PACS system is the Digital Imaging and Communications in Medicine (DICOM) format. The stored images may be transmitted digitally via the PACS system, often reducing or eliminating the need for manually creating, filing, or transporting film jackets.

The network 190 may also be connected to a Radiology Information System (RIS) 140. The radiology information system 140 is typically a computerized data storage system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a Laboratory Information System 144. Laboratory Information System 144 is typically a system which stores information created or generated by clinical laboratories. Also attached to the network 190 may be a Digital Pathology System 146 used to digitally manage and store information related to medical pathology.

Also attached to the network 190 may be a Computer Aided Diagnosis System (CAD) 148 used to analyze images. In one embodiment, the CAD 148 functionality may reside in a computing device separate from information display computing device 150 while in another embodiment the CAD 148 functionality may reside within information display computing device 150.

Also attached to the network 190 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from information display computing device 150 while in another embodiment the 3D Processing functionality may reside within information display computing device 150.

Also connected to the network 190 may be a Web Server 147.

In other embodiments, other computing devices that store, provide, acquire, and/or otherwise manipulate medical data may also be coupled to the network 190 and may be in communication with one or more of the devices illustrated in FIG. 1, such as with the information display computing device 150.

As will be discussed in detail below, the information display computing device 150 may be configured to interface with various networked computing devices in order to provide efficient and useful access to medical examination data that is stored among the various systems present in the network. In other embodiments, information display computing device 150 may be used to display non-medical information.

Depending on the embodiment, the other devices illustrated in FIG. 1 may include some or all of the same components discussed above with reference to the Information Display Computer Device 150.

Figure 1B:
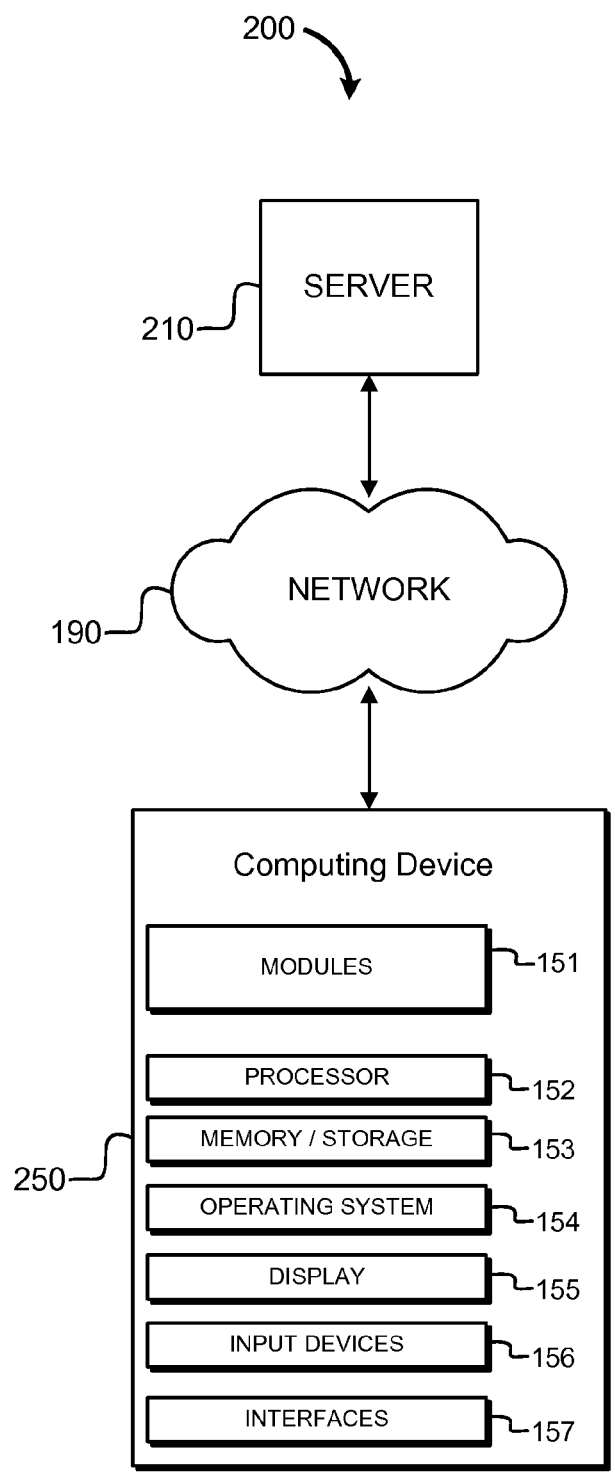

FIG. 1b is a system diagram illustrating various components of a system 200 for managing data utilizing certain systems and methods described herein. As shown, the system 200 includes a computing device 250 and may include other systems, including those shown in FIG. 2.

The computing device 250 may take various forms. In one embodiment, the computing device 250 may be a computer workstation having modules 151. In other embodiments, modules 151 may reside on another computing device, such as a web server, and the user directly interacts with a second computing device that is connected to the web server via a computer network. The modules 151 will be described in detail below.

In one embodiment, the computing device 250 comprises a server, a desktop computer, a workstation, a laptop computer, a mobile computer, a Smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 250 may run an off-the-shelf operating system 154 such as Windows, Linux, MacOS, Android, or iOS. The computing device 250 may also run a more specialized operating system which may be designed for the specific tasks performed by the computing device 250.

As with computing device 150 described herein with reference to FIG. 1a, computing device 250 may include one more computing processors 152, may include memory storage 153, may include or be interfaced to one more display devices 155, may include or be interfaced to one or more input devices 156, and/or may include one or more interfaces 157.

Computing device 250 may communicate and/or interface with other systems and/or devices via network 190, as described herein with reference to FIG. 1.

Also connected to network 190 may be a server 210 that communicates with computing device 250, for example allowing communication of images or other data (e.g., medical or non-medical data, such as e-commerce data) between server 210 and computing device 250.

FIG. 2 illustrates two mobile information display computing devices. In particular, FIG. 2 illustrates a smart phone 290 and a tablet device 295 that may each execute a mobile operating system such as iOS, Android, or Windows Mobile, or that may execute desktop computer operating systems, such as those discussed above with reference to the computing device 150. Any references herein to the Information Display Computer Device 150, or more generally to an Information Display Computer Device or simply a computing device, refer to one of any suitable computing device, including the computing devices described with reference to FIGS. 1a, 1b, and 2, as well as any other suitable computing device. The devices of FIG. 2 utilize touch screen input, but other input devices could be utilized on these devices, as well as other devices, including a computer mouse, keyboard, trackball, video or motion detection devices, etc. For example, an input device may comprise a video camera that acquires images of a user (or a portion of the user, such as a user's hands or fingers) and tracks movement of the user in order to correlate the movements with input commands. Thus, while the description herein refers primarily to input provided via a touch sensitive device, input may be provided using any other input device, including those discussed herein as well as other currently available or later developed input devices.

Example Embodiments Related to Medical Imaging

Figure 3:
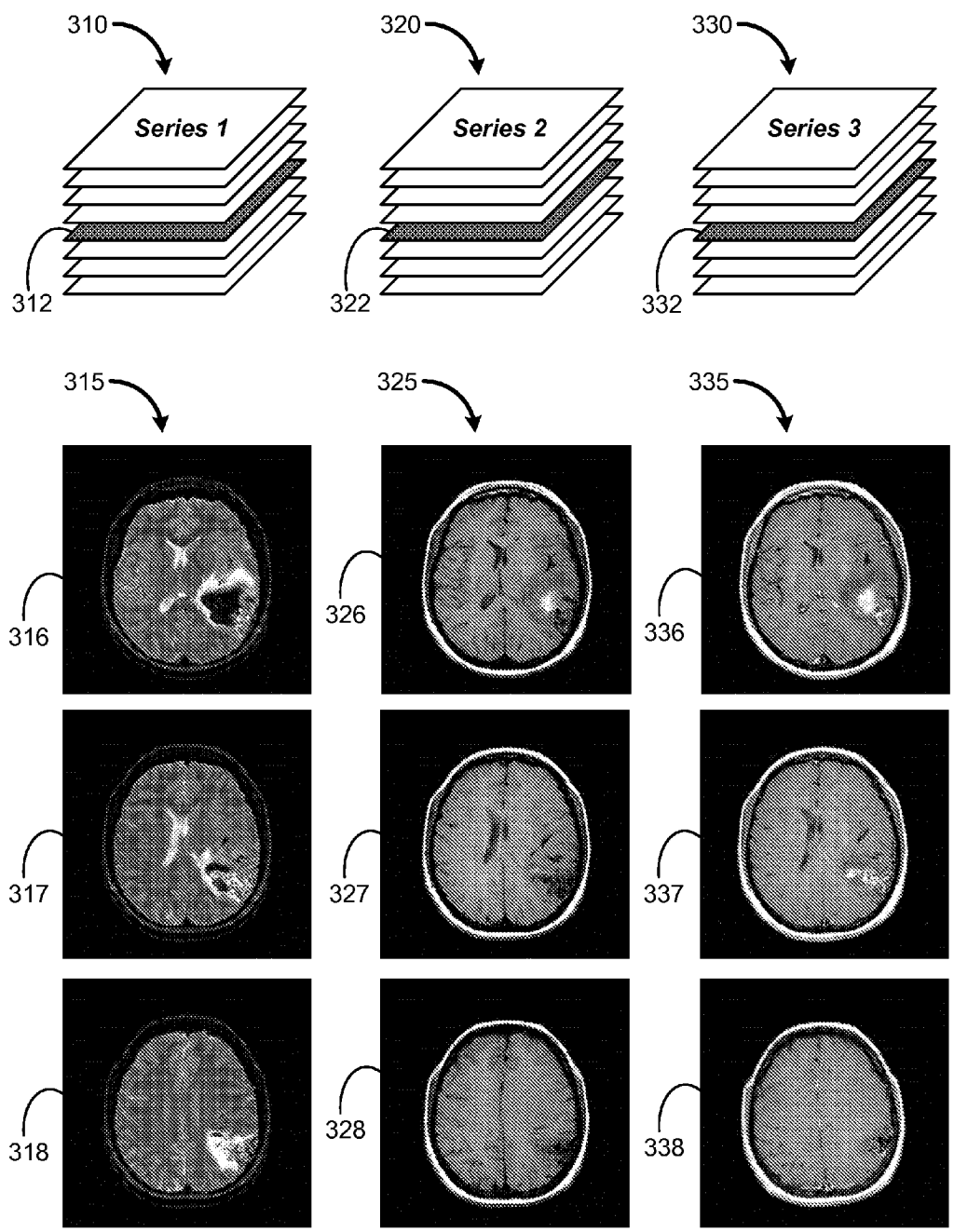
FIG. 3 illustrates three sample image series, each including multiple medical images.

FIG. 3 illustrates three sample image series 310, 320, and 330, each including multiple medical images. Medical imaging exams, such as computed tomography (CT), magnetic resonance imaging (MRI), ultrasound, nuclear medicine, positron emission computed tomography (PET), digital angiography, mammography, computed radiography, digital radiography, fluoroscopy, and others, may include hundreds or thousands of images and are commonly viewed using computing systems configured with one more display devices, such as monitors. Viewing these medical exams on handheld devices becomes problematic because of the small screen size of these portable devices. For example, because of the small screen size of handheld devices, only one or a few images can be displayed at once (at a resolution that provides useful detail). Otherwise, images are too small for people to accurately perceive. For example, the screen on the smartphone 290 of FIG. 2 is large enough to display one or at most two images at a size that would be comfortable for the user to view.

Even for devices with larger screens, such as the tablet computer 295 of FIG. 2, only a small number of images can be simultaneously displayed at a size that would be comfortable for a user to view.

Described herein are improved systems and methods for displaying and interacting with images displayed on handheld devices. In addition, the systems and methods described herein may also be applied to computing devices with larger display systems, including those with one or more computer monitors.

Medical imaging exams are typically organized into one or more image series (or simply "series"), with each series consisting of one or more images, and sometimes hundreds or thousands of images. Images in a series typically share some common characteristic, for example the type of acquisition, time of acquisition, and/or anatomic planes. For example, a brain MRI might consist of the following series:

Sagittal T1 images acquired before contrast administration
  Axial T1 images acquired before contrast administration
  Axial FLAIR images acquired before contrast administration
  Axial T2 images acquired before contrast administration
  Axial Diffusion images acquired before contrast administration
  Sagittal T1 images acquired after contrast administration
  Axial T1 images acquired after contrast administration
  Coronal T1 images acquired after contrast administration When a user is viewing a particular series, he may need to also view other exams obtained on the same patient using the same or different modalities, for example to determine if there has been a change in the size of a brain tumor. Each of these prior exams may also include one or more series. In the course of interpreting an exam, the user may need to compare images from different series, both within an exam and often across exams.

FIG. 3 illustrates three image series 310, 320, and 330 that might be acquired in an exam, in this case a brain MRI exam. In practice, the numbers of images in each series may be up to hundreds or even thousands of images and the slice thickness and slice spacing may vary from series to series within the same exam and between exams. For purposes of illustration, only a few images of each of image series 310, 320 and 330 are illustrated. Columns 315, 325, and 335 depict three example images from each of the three image series 310, 320 and 330, respectively. In this example, the following series from a brain MRI are depicted:

column 315 illustrates three Axial T2 images 316, 317, and 318 of image series 310 acquired before contrast administration
  column 325 illustrates three Axial T1 images 326, 327, and 328 of image series 320 acquired before contrast administration
  column 335 illustrates three Axial T1 images 336, 337, and 338 of image series 330 acquired after contrast administration Images in a particular column (e.g., images 316, 317, and 318) are taken at different spatial positions (e.g., images 316, 317, and 318 are three consecutive images of the Axial T2 series obtained at different spatial positions). Images in a particular row (e.g., images 317, 327 and 337) depict images of different series that were obtained at the same (or similar) spatial position.

When viewing exams such as those illustrated, particularly on small devices where it is practical to display only a portion of an image, one image, or a small number of images, it would be advantageous when changing between first and second image series (e.g., between series 310 and 320) to automatically select for display an image from the second series that is at substantially the same anatomic position as the currently displayed image in the first series. Systems and methods described herein provide that functionality. For example, if the user were viewing an image in one series, e.g., image 317 in series 1, located at position 312 in the series 310, based on systems and methods described herein, when the view is changed to a different series, e.g., image series 320, the image at the same spatial position as image 317 would be selected and presented, e.g., image 327 would be presented in place of image 317. If the view is then switched to the series 330, the image in the corresponding anatomic position would be presented, in this example image 337.

Generally, series within the same exam are acquired with the patient in the same position. Therefore locating images from different series that correspond to the same spatial position may be performed by selecting images at the same position within the respective image series. However, when series are from different exams, the numerical frame of reference may differ. In order to correlate the position of images from series with different frames of reference, the different exams need to be spatially registered. This can be accomplished manually or automatically with various techniques known in the industry.

Figure 4:
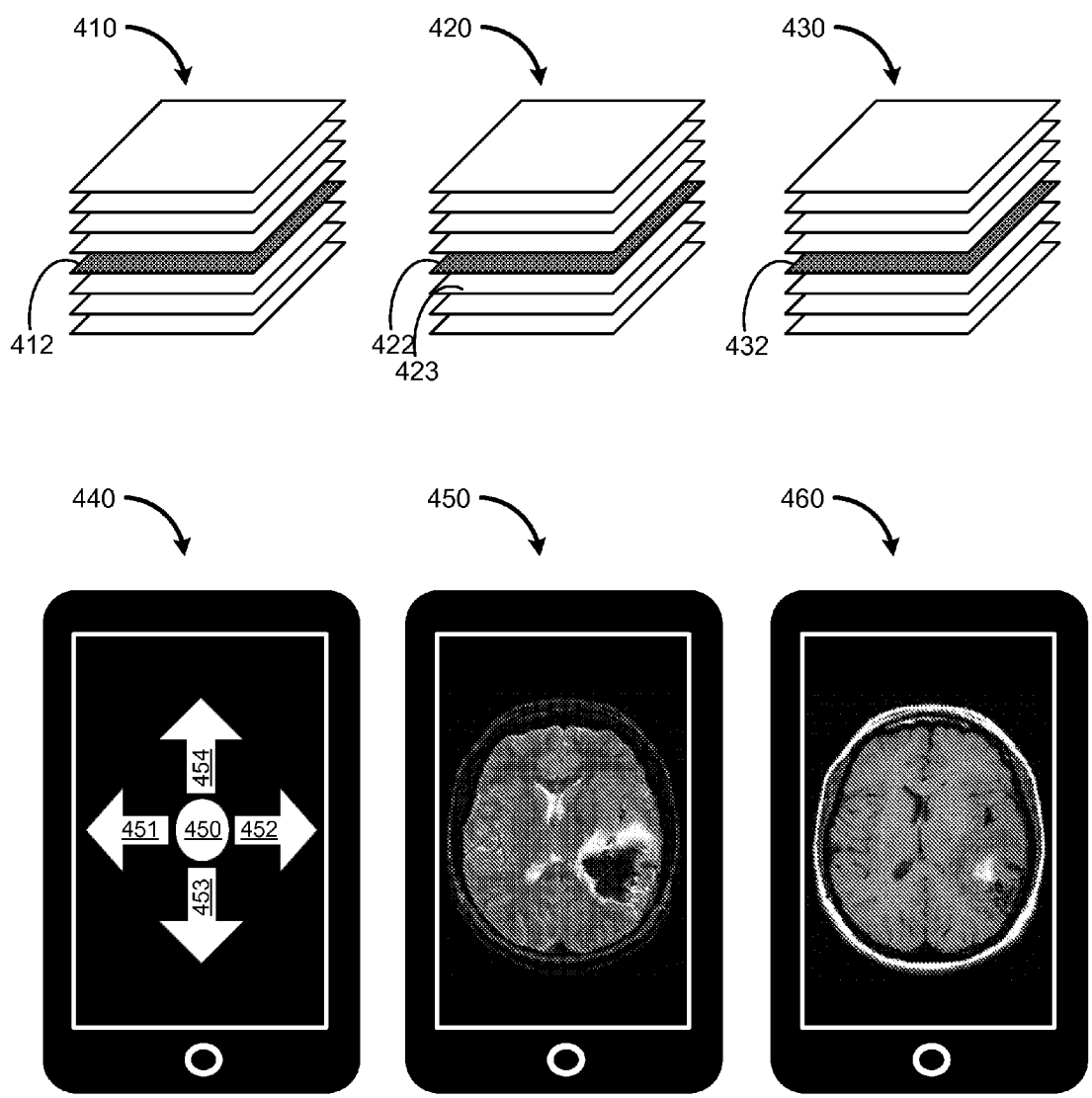
FIG. 4 illustrates three image series each including multiple images that can be selectively displayed on a mobile computing device.

FIG. 4 illustrates three image series 410, 420, 430 each including multiple images that can be selectively displayed on a mobile computing device. In view 440 the mobile computing device, such as a touch screen device, is shown with white arrows on the screen illustrating potential gestures that a user might utilize in order to navigate between images of the image series 410, 420, 430. In this embodiment, in response to the user touching the screen at an arbitrary position, for example position 450, and moving his finger to the left or right, illustrated by arrows 451 and 452, the software executing on the mobile computing device would interpret the movement as a command to navigate between image series, essentially moving from one image series to an adjacent image series.

For example, view 450 illustrates the handheld device displaying a T2 weighted image 422 from a brain MRI, e.g., from the series 420. In response to the user touching the screen and moving his finger to the right, the handheld device causes the display to be updated to show a corresponding image from another series, in this example the series 430. In this example, this action would result in display of a T1 weighted image 432 of the brain, shown in view 460, which is at the same anatomic position as the T2 weighted image 422 that was previously displayed (shown in view 450). Similarly, in response to the user touching the screen at some arbitrary position and moving his finger up or down, illustrated by arrows 453 and 454 of view 440, the handheld device would cause the display to change to another image within the current series, essentially moving up and down within the stack. For example, if the user provides a downward motion while image 422 of images series 420 is displayed, the display may be updated to show adjacent image 423 of image series 420. Depending on the embodiment, navigation between images within a series, as well as navigation between image series, may be performed in response to various user interactions. For example, in another embodiment movements left and right (e.g., directions indicated by arrows 451, 452) may cause movement between images in a particular series, while movements up and down (e.g., directions indicated by arrows 453, 454) may cause movement between anatomically common images in different image series.

Figure 5:
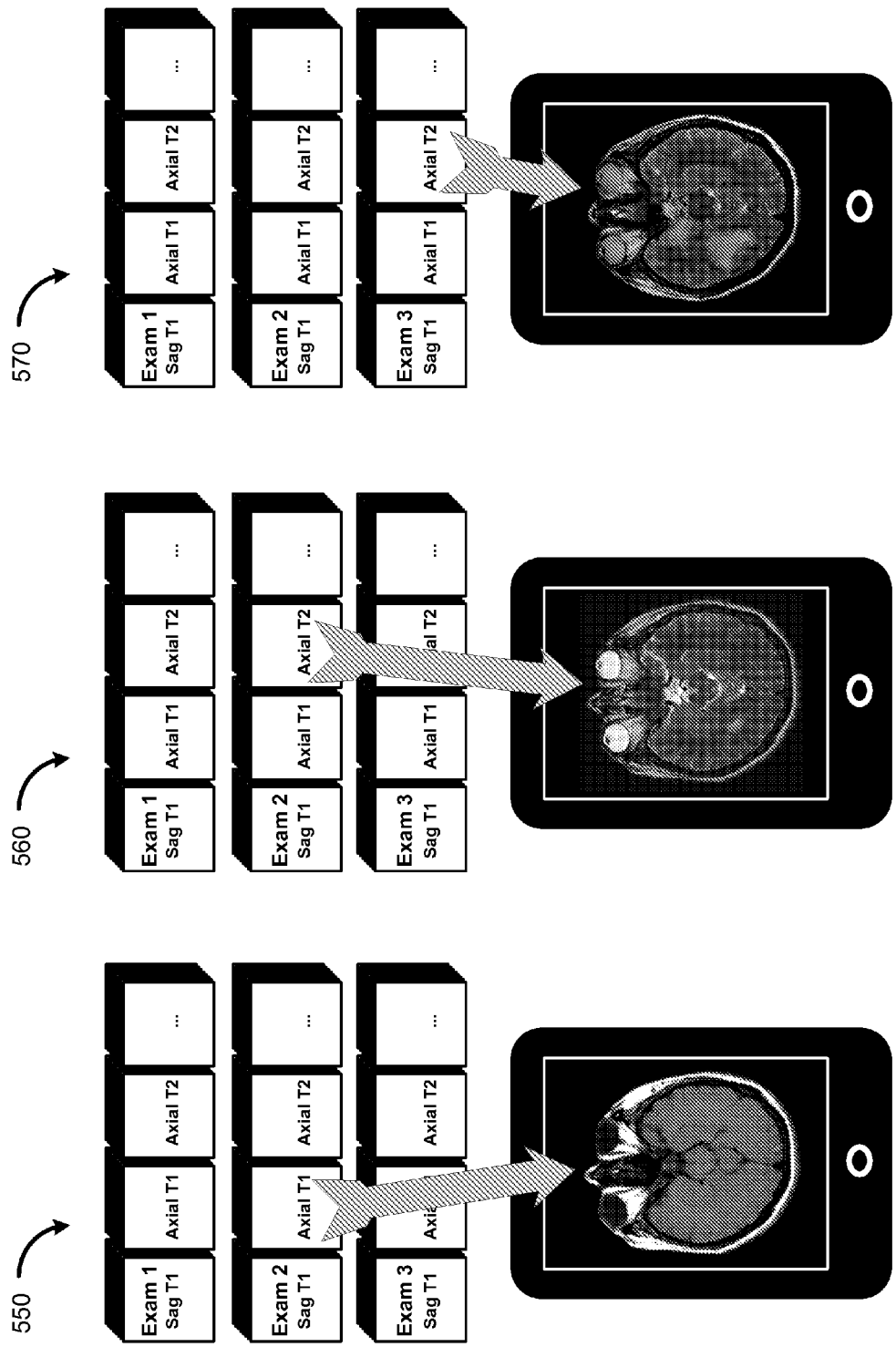
FIG. 5 illustrates navigation between image series of multiple exams according to one embodiment.

FIG. 5 illustrates an embodiment where the systems and method described herein are applied to cases where there are multiple exams. Column 550 illustrates a series of image stacks where each image stack represents a series of images. In particular, column 550 illustrates three exams, with each exam including multiple series including a "Sag T1", "Axial T1" and "Axial T2" exemplary series within a brain MRI in this example. In column 550, an image from the Axial T1 series of Exam 2 is displayed on the computing device, illustrated by a hatched arrow connecting that series and the computing device.

With an image from the Axial T1 series of Exam 2 displayed, the user may request display of an anatomically corresponding image from the axial T2 series of the same Exam 2. For example, the user may request images from a different series of a same exam by performing a predetermined (or user customizable) action on a touch screen display, or providing any other input on an available input device, such as a mouse, keyboard, touch pad, microphone, camera, etc. Using the systems and methods described herein, in response to the user providing a request for display of a different series, in this case the T2 series, the T2 image at the same spatial location as the previously displayed image is automatically displayed. Column 560 illustrates the computing device display after it is updated to show the Axial T2 image of Exam 2 that is at the same spatial location as the previously displayed Axial T1 image of Exam 2.

The computing system may also navigate between images of corresponding anatomical positions (or the closest anatomical position available) between different exams. For example, column 570 illustrates display of an Axial T2 image from a different exam, Exam 3. Navigation between exams may be performed via a predetermined (or user customizable) action or input, such as a touchscreen motion in a direction that is orthogonal to the direction used to navigate between images of different series within a same exam (e.g., movement between the images shown in columns 550 and 560). Thus, a user can navigate directly from an image in the axial T2 series of Exam 2 (e.g., column 560), to an image in the Axial T2 series of Exam 3 (e.g., column 570) that represents the same spatial position, wherein the image of the Axial T2 series of Exam 3 is automatically selected and presented by the computing system, without the need for the user to scroll through other images of either Exam 2 or Exam 3 in order to identify the corresponding image.

In the embodiment of FIG. 5, in response to receiving user input instructing movement from one exam to another, the computing device selects an image in the newly selected exam from the same series type (e.g., the Axial T2 series in columns 560 and 570) and spatial position as the previously displayed image.

Figure 6:
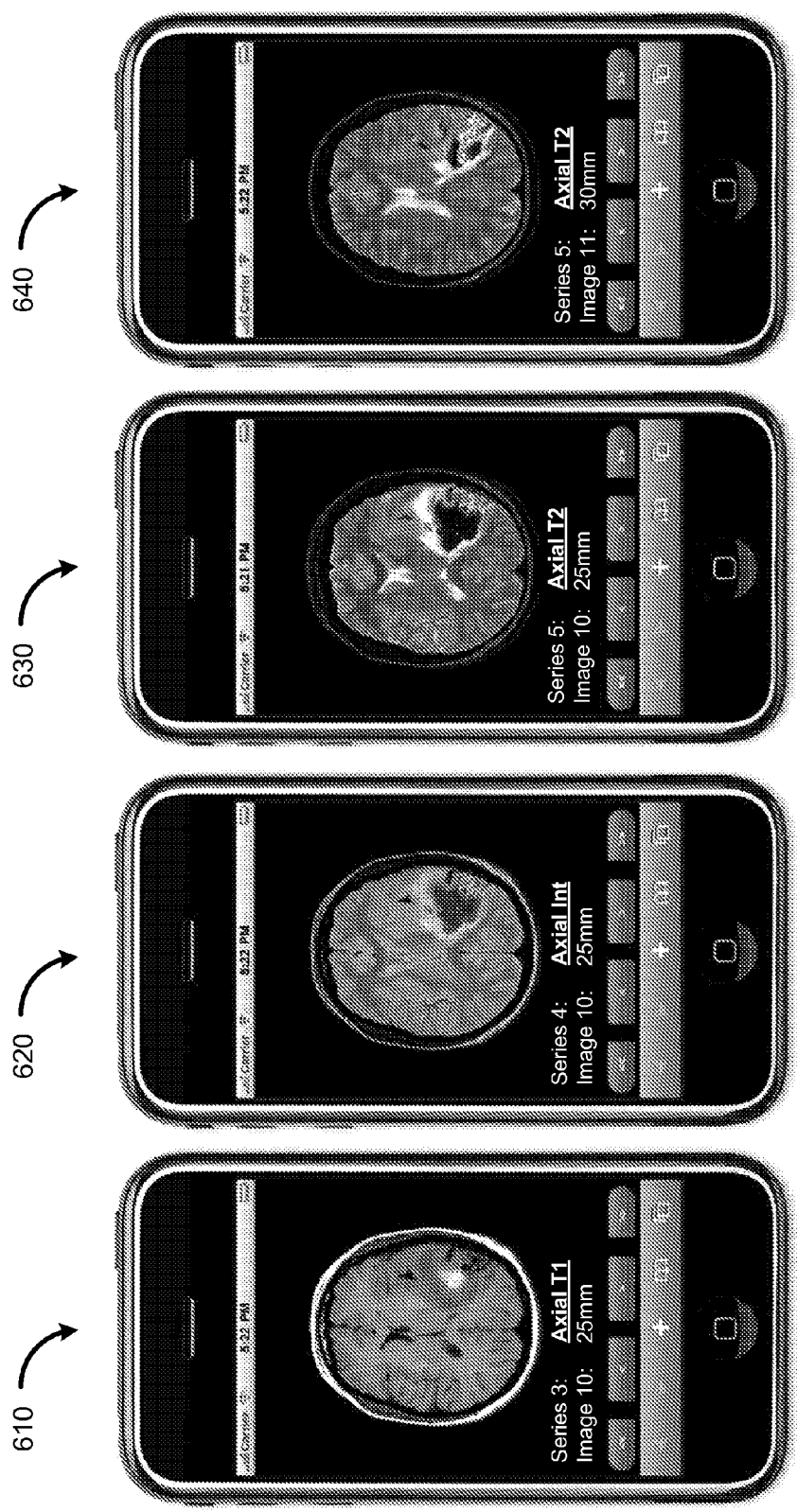
FIG. 6 illustrates a touchscreen device depicting various images in response to received navigation commands.

FIG. 6 illustrates a touchscreen device depicting various images in response to received navigation commands. In this embodiment, the touchscreen mobile device, such as an iPhone or Android device, displays an image from a series as well as navigation buttons labeled as "<<", "<", ">", and ">>". In this embodiment, the user may be able to navigate between image series with two different actions. The user can touch the screen and flick his finger to the left or touch the "<<" button to display the prior series within the group of available series. Similarly, the user can touch the screen and flick his finger right or touch the ">>" button to display the next series within the group of available series.

In the example illustrated in FIG. 6, images from three of the series in the example exam are shown, series 3 (Axial T1), series 4 (Axial Int) and series 5 (Axial T2). Consecutive views show the appearance of the device in response to user input, as described below.

View 610 shows the handheld computing device displaying image 10 from Series 3 (Axial T1).

View 620 shows the device after the user has provided input to advance to the next series, in this case Series 4, the "Axial Int" series. Note that the image displayed is in the same anatomic position as the image displayed in the previously displayed series in view 610. In this particular exam, numbered images within each series have corresponding spatial positions, with image 10 within each series corresponding to a spatial position along the axis of the patient's body of "25 mm", as shown in image labels within the views. However, in other embodiments the same image number in different image series may not correspond to a same anatomical position of a patient. Thus, in some embodiments, the corresponding images in different image series may have different image numbers. In some embodiments, the computing device, or a networked computer device in communication with the computing device that displays the images, automatically determines the appropriate matching image in a newly selected image series, such that the user is not required to manually select a matching image.

View 630 shows the device after the user has provided input to advance to the next series, in this case Series 5, the "Axial T2" series. Note that the image displayed is in the same spatial position (and same image number in this example) as the image displayed in the previously displayed series of view 620.

In this embodiment, the user can change the image displayed within the current series with one of two different actions. In particular, the user can touch the screen and flick his finger down or touch the "<" button to display a lower numbered image in the currently displayed series and, likewise, can touch the screen and flick his finger up or touch the ">" button to display a higher numbered image in the currently displayed series. In other embodiments, other user inputs may be used to control movement between images of a currently selected image series and/or movements between different image series.

View 640 shows the device after the user has provided input to advance to the next image within the current series, such as by flicking his finger up or touching the ">" but in the embodiment of FIG. 6. Note that the series has not changed from view 630 to 640 and remains at Series 5 (Axial T2), but the image number has advanced from image 10 to image 11. Note that image 11 is at position 30 mm while image 10 was at 25 mm.

Figure 7:
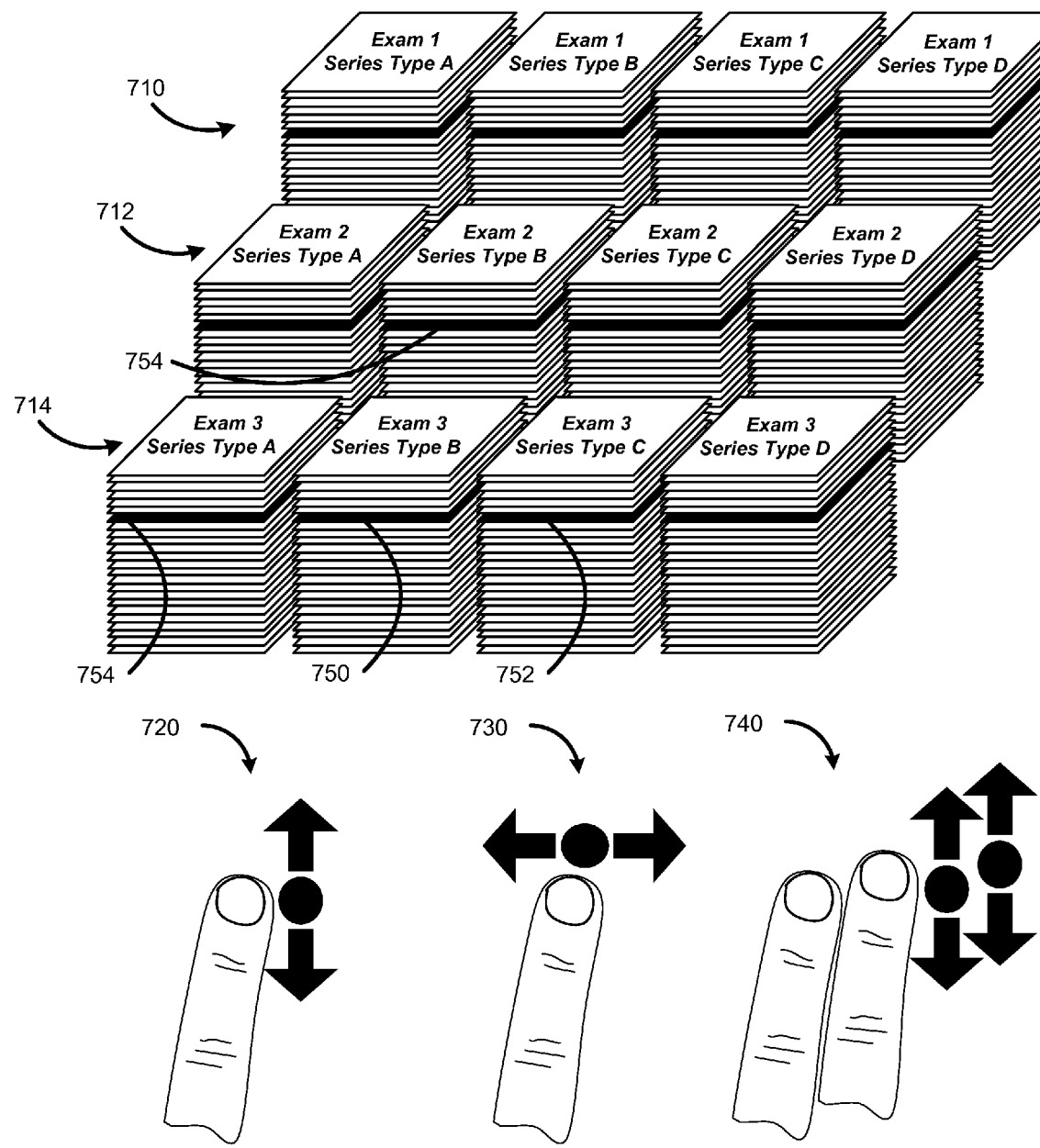
FIG. 7 illustrates interactions that a user might use on a computing device with a touch sensitive input device to navigate among one or more exams, each with one or more image series that may each include one or more images.

FIG. 7 illustrates interactions that a user might use on a computing device with a touch sensitive input device (e.g., a touchscreen or touchpad) to navigate among one or more exams, each with one or more image series that may each include one or more images. In particular, FIG. 7 illustrates three example exams 710, 712, and 714, each including four series labeled as series types A, B, C, and D. In an MRI exam, for example, series types might differ based on:

Plane of acquisition, e.g., sagittal, axial, coronal, oblique, etc.

Pulse sequence, e.g., T1, FLAIR, T2, diffusion, MRA, MRV, etc.

Slice thickness and slice spacing 2D vs. 3D volumetric acquisition

Whether they were acquired before or after intravenous contrast administration, e.g., unenhanced or enhanced.

Primary acquired images or secondary reconstructed images. Reconstructed images might be images that were created from acquired images using techniques such as volumetric rendering, MPR (multiplanar reformatting), MIP (maximum intensity projection), etc.

Views 720, 730, and 740 illustrate user interaction that are interpreted by certain computing devices, such as the mobile computing device of FIG. 6, as requests to navigate among images, series, and exams.

View 720 illustrates an interaction that a user might use to request display of different images within a series. In this embodiment, the user employs up-down finger motions to choose different images within a series. For example, if a computing device is currently displaying an image from Series Type A of Exam 3 and the user provides an up or down finger motion, another image (e.g. an adjacent image) from Series Type A of Exam 3 would be displayed on the computing device. In the case of series in which images within the series represent different spatial positions, changing images may result in changing the anatomic position displayed. In the case where the images in a series represent different times, such as ultrasound or MRI images depicting a cardiac cycle, moving to different images within the series may change the time of the image displayed without changing its anatomic position. In other examples, the images within a series may represent different projections, for example AP, Lateral and Oblique view of the cervical spine obtained with digital radiography. In other examples, the images in a series may represent different reconstructed images, for example using multiplanar reformatting, maximum intensity projection imaging, or 3D volumetric display.

View 730 illustrates an interaction that a user might use to request display of an image from a different series than is currently displayed. In this embodiment the user employs left-right finger motions to navigate among different series within an exam, correlating with moving laterally within stacks of images of different image series within an exam. For example, if image 750 of Series Type B in Exam 3 is currently displayed and the user provides a movement to the right on a display of the computing device, the computing device may move to adjacent Series Type C of Exam 3 and display image 752. Advantageously, as the user navigates between image series, the anatomic position of the image presented does not change, even though images are presented from different series. Thus, instead of displaying a top image of Series Type C of Exam 3 in response to the user navigating to that series from image 750 of Series Type B of Exam 3, the computing system selects the image of Series Type C of Exam 3 that is at the same anatomic position, e.g., image 752, for display. Images in the other series of Exam 3 that correspond to images 750 and 752 are also illustrated as black images. Similarly, a sample image of corresponding anatomy is illustrated as a black image in each of the series of Exams 1 and 2.

View 740 illustrates an interaction that a user might use to navigate among different exams. In the embodiment illustrated, the user touches the screen with two fingers simultaneously and moves them together up or down, changing the exam being displayed. Employing systems and methods described herein, changing exams causes display of the corresponding image from the new exam, with both the same series type and anatomic position. Thus, referring to column 560 of FIG. 5, the user was viewing an image from a T2 series of Exam 2. The user might employ the multitouch action illustrated in view 740 of FIG. 7 to display an image from a different exam, such as Exam 3. Using systems and methods described herein, the computing device may automatically select an image of Exam 3 that is from the same series type, in this example "Axial T2", and is in the same anatomic position as the image that was being displayed from the first exam. With reference again to FIG. 7, if image 750 of Series Type B in exam 3 is currently displayed and the user provides an upward two-finger movement, the computing device selects an image from a different exam, e.g. Exam 2, and selects an image from that different exam that is from the same series type, e.g., Series Type B, and is of the same anatomical position as is currently viewed. Thus, the upward two-finger movement from image 750 may cause image 754 of Exam 2 to be displayed on the computing device.

In other embodiments, other user inputs than those discussed above may be used to navigate between images in different series of a same exam, between images in a, and/or between different exams. For example, in one embodiment a single finger motion up or down indicates navigation between different series within an exam, while a single finger motion left or right indicates movement to adjacent images in a currently selected in series. In other embodiments, buttons may be provided to allow the user to navigate between images, series, and exams. Similarly, gestures or other input commands may be used to provide such instructions to a computing device. In one embodiment, the inputs that correspond to each navigation feature can be customized by a particular user.

Example Image Navigation Method

Figure 8:
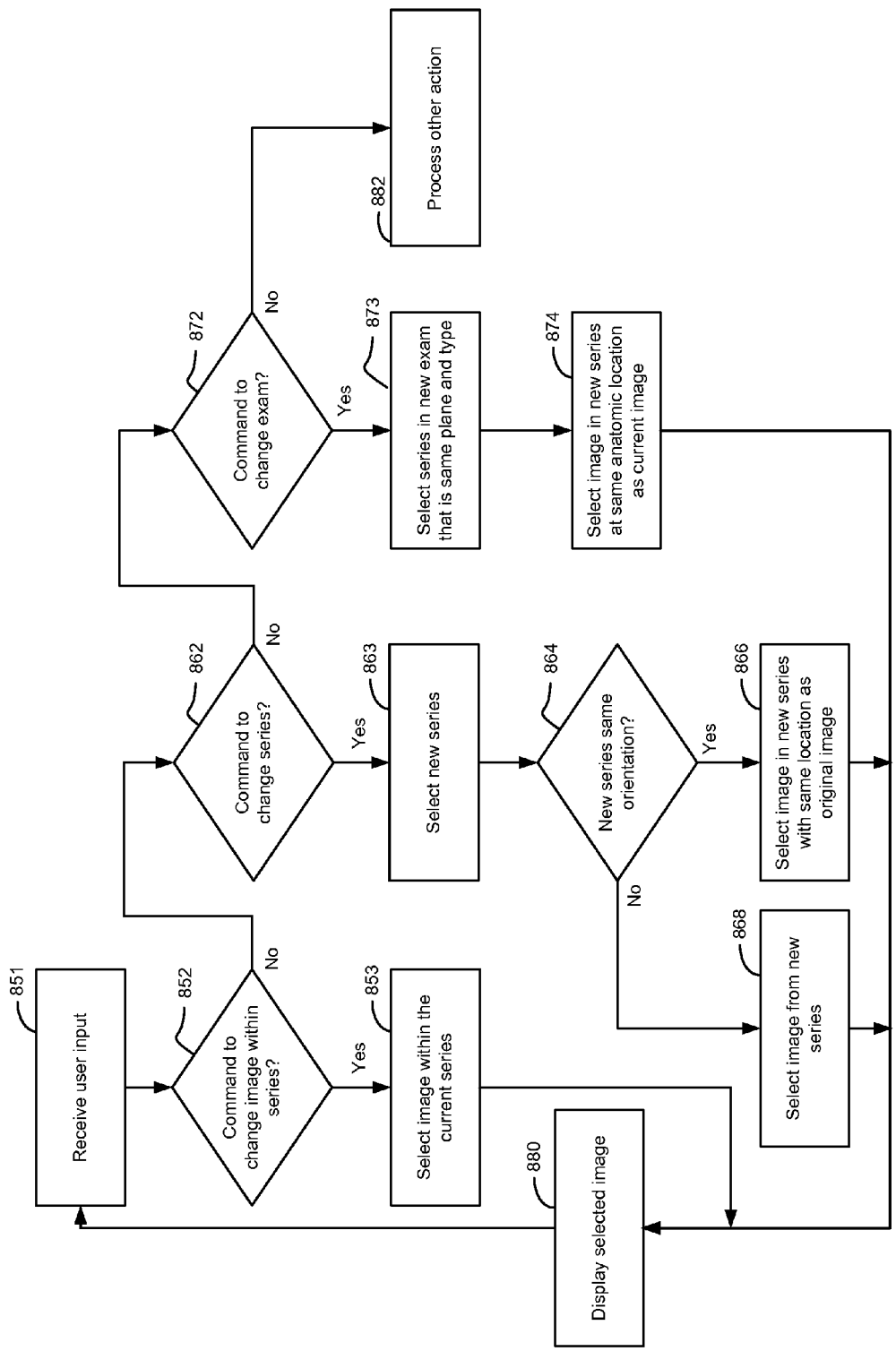
FIG. 8 is a flowchart of one embodiment of a method for navigating between images of multiple series and/or exams.

FIG. 8 is a flowchart of one embodiment of a method for navigating between images of multiple series and/or exams. Depending on the embodiment, the method of FIG. 8 may include fewer or additional blocks and/or the blocks may be performed in a different order than is illustrated. Software code configured for execution on a computing device in order to perform the method of FIG. 8 may be provided on a tangible computer readable medium, such as a compact disc, digital video disc, flash drive, hard drive, memory device or any other tangible medium. Such software code may be stored, partially or fully, on a memory of a computing device, such as the computing devices 150, 250, and/or other computing devices illustrated in the Figures, in order to perform the method outlined in FIG. 8 by those respective devices. For ease of explanation, the method will be described herein as performed by a computing device, which should be interpreted to include any one or more of the computing devices noted above and/or any other suitable computing device.

Beginning in block 851, input is received from a user. Depending on the embodiment, the input may be received via a touch sensitive surface of a computing device, or through any other input means. For example, in one embodiment voice commands are recognized by the computing device and may be used to initiate navigation between images. For purposes of illustration, the various user inputs that may be received in block 851 are referred to as user "commands." Thus, a finger swipe to the left provides a first command, a finger swipe to the right provides a second command, and a double finger swipe up, down, or from side to side each provide separate commands.

Next, in block 852 the computing device determines whether or not the command is to change images within a series. For example, commands to navigate between images in a series may be associated with the interactions illustrated in view 720 of FIG. 7. In other embodiments, commands to navigate between images in the series may be associated with other user inputs. If the computing device determines that a command to navigate between images in the series has been received, the method continues to block 853 where the computing device selects an appropriate next image of the current series for display, and then to block 880 where the computing device updates the display to include that selected next image, and then to block 851 where further user input may be received.

If the computing device determines that a command to navigate between images in the current series has not been received at block 852, the method moves to block 862 wherein the computing device determines whether a command to change series, for example using the interaction illustrated in view 730 of FIG. 7, has been received. If the computing device determines that a command to change series has been received, the method continues to block 863 where the computing device selects another series from which an image will be selected for display. In one embodiment, the newly displayed series may be automatically selected from the undisplayed series so that the newly displayed series is in the same plane (or substantially the same plane) as the currently displayed series.

In one embodiment, commands for navigation between image series may be provided by the user interaction indicated in view 730 of FIG. 7, for example. In other embodiments, commands for navigation between image series may be provided via any other input means. Next, in block 864 the computing device determines whether or not the new series has the same orientation as the original series, for example axial, coronal, sagittal or the same oblique orientation. If yes, then in block 866 the image in the new series at the same location as the currently displayed image is automatically selected for display. With reference to FIG. 7, with image 750 displayed on the computing device, a command to change series may cause the computing device to select image 752 of an adjacent series (e.g., in response to a finger swipe to the right) or image 754 of an adjacent series (e.g., in response to a finger swipe to the left).

If the computing device determines at block 864 that the new series is not the same orientation as the current series, the method moves to block 868, where an image from the new series is automatically selected. In some embodiments, the first image of the new series is selected at block 868. In other embodiments, an image within a series is selected based on user preferences, for example the middle image. In another embodiment, the image selected is in the same location as the image from the most recently displayed series in that plane. For example, if a sagittal T1 weighted series is displayed with the location of the image 15 mm to the right of midline and a user selects an axial series and then subsequently selects a sagittal series, such as a sagittal T2 series, an image within the sagittal T2 series may be automatically selected that is also at 15 mm to the right of midline. Once an image is selected in either block 866 or 868, the method continues to block 880 where the computing device updates the display to include the selected image, and the method then returns to block 851 where further user input may be received.

If the computing device determines that a command to navigate between series has not been received at block 862, the method moves to block 872 where the computing device determines whether a command to change exams has been received. If yes, the method moves to block 873 where a new exam is selected and the exam is analyzed to identify a series that matches the type of the current series. For example, if the current series is an axial T1 performed after contrast administration, then the new exam is searched for a similar series. Once the matching series is selected, the method moves to block 874 where the selected new series is searched for an image that is closest in location to the current image. Once an image is selected in block 874, the method continues to block 880 where the computing device updates the display to include the selected image, and then returns to block 851 where further user input may be received. In some embodiments, the method of FIG. 8 may not include blocks 872, 873, and 874. For example, in the case where a user navigates between multiple images of multiple series within a single exam, blocks 872, 873, and 874 are not necessary.

If the computer device determines at block 872 that a command to change exams has not been received, the method continues to block 882 where some other action may be performed by the computing device. For example, user input other than image navigation commands may have been received and, accordingly, actions associated with those other user inputs may be performed at block 882. Alternatively, no action is performed by the computer device at block 882 other than causing the computing device to listen for additional user input, such as by returning to block 851.

The method of FIG. 8 illustrates analysis of user input in a sequential fashion, e.g., processing block 852, then block 862, then block 872. However, these blocks may be performed in different orders and/or may be performed concurrently, such that a command to change the exam (block 872) may be identified by the computing device without first determining whether a command to change an image within the current series (block 852) or a command to change series (block 862) has been received.

Figure 9:
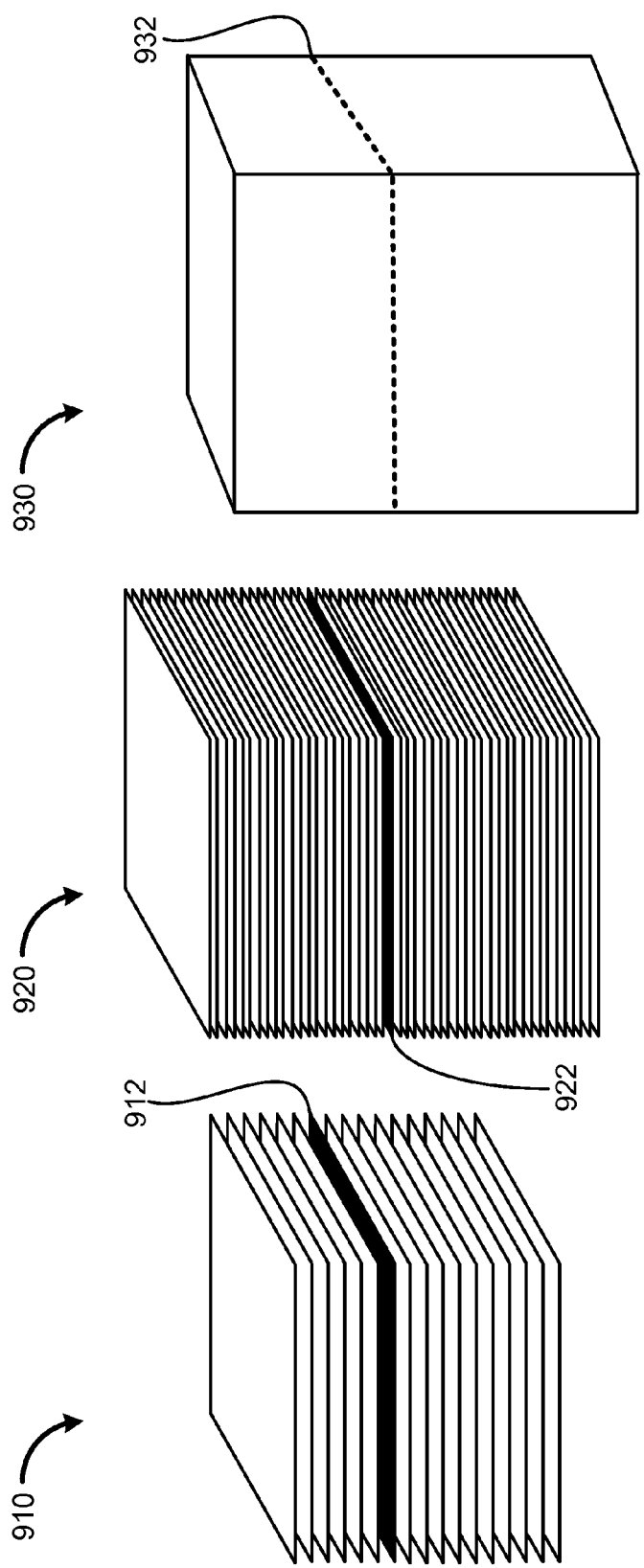
FIG. 9 illustrates three example image series.

FIG. 9 illustrates image series 910, 920, and 930. In this embodiment, image series 910 comprises a first series of images with an arbitrary number of images, slice thickness, and slice spacing and image series 920 comprises a second series of images that are within the same plane as the images of the image series 910. However the number of images, anatomic coverage, and slice spacing of images in series 920 is different than those in series 910. Additionally, while slice thickness is not graphically illustrated in series 910 and 920, slice thickness may differ between the two series as well.

In some embodiments, when a user navigates between the image series 910 and 920, an image from the second image series 920 is automatically chosen so that it matches (as closely as possible) the anatomic position of an image in the first image series 910, both in terms of the 3D orientation of the imaging plane as well as the spatial position of the plane. In this embodiment, selecting an image from the second image series 920 that matches an image in the first image series 910 may not require that the images within the series have the same number of images, same slice thickness, or same slice spacing. Additionally, matching images in the first and second image series may have different anatomic coverage with at least some overlap.

In matching images between the series, the closest anatomic match may be chosen. For example, if image 912 is the image being displayed and the user switches to series 920, image 922 may be automatically selected for display because it is in the same spatial position (or the closest spatial position) as image 912.

In other embodiments, one or both of the series may be volumetric acquisitions or a series of 2D images that may be treated as a volumetric acquisition. For example, the series 930 is a volumetric acquisition or series of 2D images acquired in any plane and treated as a volumetric acquisition. In matching an image from the volumetric acquisition shown in series 930 to images of other series, such as images of series 910 and 920, an image may be automatically reconstructed using the volumetric data using techniques such as multiplanar reconstruction (MPR) in order to construct an image in the same plane and spatial position as images in other series. Depending on the embodiment, the slice thickness of the reconstructed image may be the same as or different than the image to which the reconstructed image was generated to match. In the example of FIG. 9, an image reconstructed in the plane depicted by the dotted lines 932 correlates with the anatomic plane and spatial position of images 912 and 922 of series 910 and 920. Thus, using the navigation techniques discussed above, a user may easily move between images 912, 922, and 932 to view images in each of the image series that are at corresponding spatial positions and planes.

Figure 10:
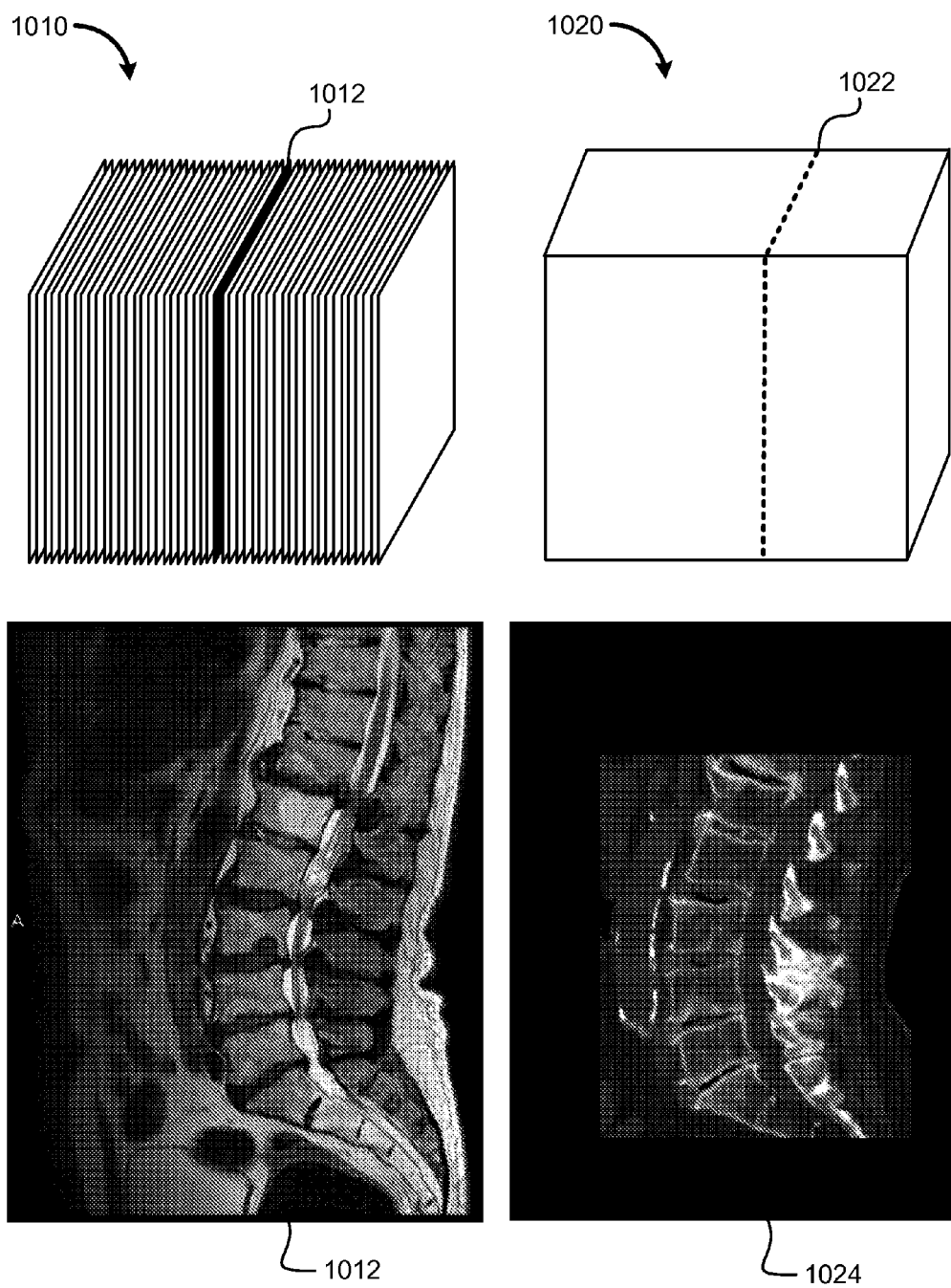
FIG. 10 illustrates a 2D image series and a 3D volumetric acquisition from which images can be constructed and displayed.

FIG. 10 illustrates a 2D image series 1010 and a 3D volumetric acquisition 1020 from which images can be constructed and displayed. In this embodiment, image series 1010 comprises images at different anatomic positions, in this example a Sagittal T2 weighted series from a lumbar spine MRI. Within the stack illustrated in series 1010, image 1012 has been selected, and is depicted as black to indicate the particular image selected. A reproduction of a sample actual image 1012, which comprises an example sagittal T2 weighted image of the lumbar spine, is depicted below the image series 1010.

In the embodiment illustrated, the user desired to correlate exams that were not only obtained at different times but which are of different modalities and acquisition types. In particular, the example series 1010 comprises an MRI acquired as a 2D acquisition while the example volumetric acquisition 1020 is a CT volumetric acquisition. Using the techniques of MPR (or similar techniques), an image may be mathematically reconstructed in any plane and with any slice thickness. Based on systems and methods described herein, a plane and slice thickness for reconstruction of an image from volumetric acquisition 1020 that matches image 1012 of series 1010 is determined and the image is generated. In this example, the computing system determined that the plane of the matching reconstructed image is along plane 1022, and the resultant reconstructed image is shown as image 1024. Thus, using the systems and methods described herein, matching images from any type of acquisition could be determined and selected for display (e.g., concurrent display) on a display device in order to enhance the viewing experience of the user. For example, one acquisition could be 2D and the other 3D, both acquisitions could be 2D, or both acquisitions could be 3D volumetric acquisitions. In other embodiments, the series could be from the same or different modalities and could be from the same or different exams. In other embodiments, a matching image or plane from which to construct an image in a newly selected series is determined based on any other characteristics of the current image/series/exam and/or selected image/series/exam.

Figure 11:
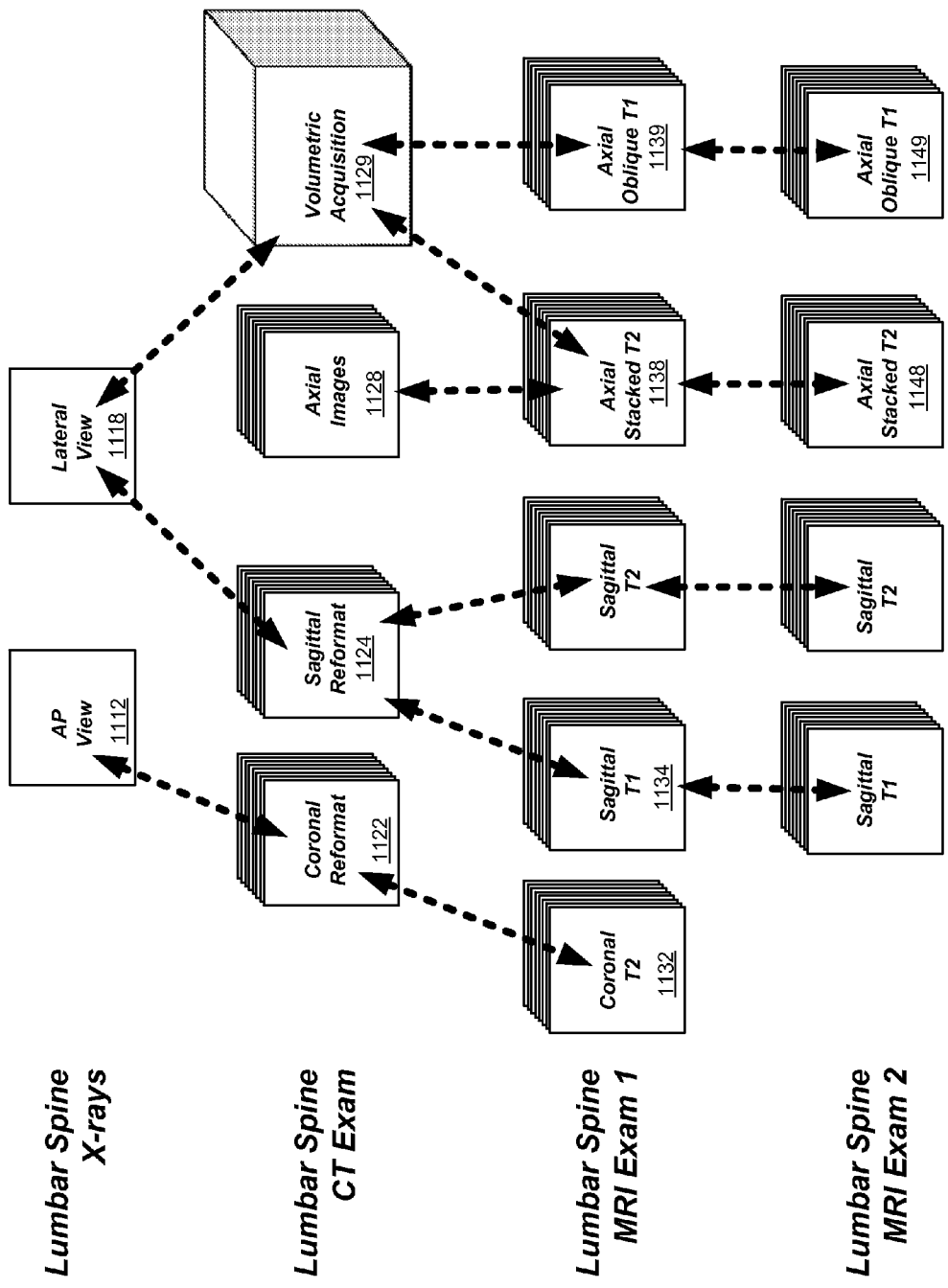
FIG. 11 is a diagram illustrating sample correlations between series types that may be used by a computing device displaying medical images in order to select a series type for display in response to a series change command from another image series.

FIG. 11 is a diagram illustrating sample correlations between series types that may be used by a computing device displaying medical images in order to select a series type for display in response to a series change command from another image series. In medical imaging, images within a series may differ in various ways, such as, for example:

Anatomic location, slice thickness, and/or slice spacing, e.g., a series of 3 mm thick MRI images obtained every 4 mm.

View or projection, e.g. AP, left lateral, right lateral, right anterior oblique.

Time, e.g., within a cardiac cycle

In addition, images within a series may vary in type, such as, for example:

Projection images, e.g., a lateral view of a lumbar spine using CR (computed radiography)

2D images, e.g. a series of contiguous 3 mm axial CT images of the brain 3D volumetric acquisition, e.g. a series of contiguous 0.6 mm axial images after contrast administration as part of a brain CTA exam.

In some embodiments, images from series of the same type are correlated. For example, in FIG. 11, series from two Lumbar Spine MRI exams (the last two rows in FIG. 11) are correlated. Because these exams have matching series types, the various series types of the first exam can be correlated with the same series type of the second exam. Such correlations between the series types of these two exams are illustrated by dotted lines between the two exams.

In other cases, a user may navigate between images of first and second exams that don't have the same series types as part of their respective image series. In such a case, series of different types may be automatically matched such that the user is presented with an image of a most closely related image series in the new exam. For example, there may be matching of:

Coronal MRI to Coronal CT reformatted images (e.g., a series change command from the Coronal T2 series 1132 of MRI Exam 1 may cause a corresponding image in the Coronal Reformat series 1122 of the CT Exam series to be selected and displayed).

Sagittal MRI to Sagittal CT reformatted images (e.g., a series change command from the Sagittal T1 series 1134 of MRI Exam 1 may cause a corresponding image in the Sagittal Reformat series 1124 of the CT Exam series to be selected and displayed).

Axial MRI to Axial CT images (e.g., a series change command from the Axial Stacked T2 series 1138 of MRI Exam 1 may cause a corresponding image in the Axial Images series 1128 of the CT Exam series to be selected and displayed).

In the embodiment of FIG. 11, the MRI Exams each include axial oblique image series (1139 and 1149) that have no closely matching images available in that plane in the CT exam. However, the CT exam includes a volumetric acquisition 1129 from which multiplanar reformation of images may be performed in order to automatically reconstruct images at the matching angle, anatomic position, and/or having other matching characteristics of images from the MRI exams. As shown in FIG. 11, MPR of the volumetric acquisition 1129 may be used to generate images associated with images from other series types, such as the lateral view series 1118 of the lumbar spine x-rays, and both Axial Stacked T2 (e.g., series 1138 and 1148) and Axial Oblique T1 (e.g., series 1139 and 1149) image series, as well as other image series in other embodiments. For example, MPR could be used with a volumetric acquisition, if available, to create a lateral, AP or other projection image dynamically.

In the case of projection images, there may be several possible matches. For example, it may be natural to match lateral projection view (e.g., Lateral view 1118) with sagittal images (e.g., Sagittal Reformat series 1124) as lateral projection images are images where projection is perpendicular to the plane of the sagittal images. The same may be true of coronal images (e.g., Coronal Reformat 1122) and AP projection images (e.g., AP View 1112).

In one embodiment, the associations between various series types, such as series types of different exams, may be stored in a data structure that is accessible to the computing device on which medical images are displayed. Thus, when commands are received to display images from other exams, the associations may be accessed in order to determine an image series of the selected exam from which an image should be displayed. Advantageously, the user viewing images from multiple exams, such as on a mobile device, is not required to navigate through multiple image series of an exam in order to locate an image and/or image series that matches the previously displayed image. In other embodiments, associations between series types, such as those illustrated in the example of FIG. 11, may be stored in a rules format. Depending on the embodiment, the associations between series types of various exams may be preset, such as by a manufacturer of image viewing software, and/or the associations may be programmable by the user. Thus, users may establish new associations between series types and/or update associations between series types according to preferences. Accordingly, different users may have associations that vary, such that navigation between a first series type of the first exam type and a second exam type by two different users results in selection of images from different image series of that second exam type. The associations may be stored in any available data structure such as in a database, a spreadsheet, script code, a flat file, and the like.

Image Navigation—Cardiac Imaging Example

As noted above, image series may contain images that differ from one another in various ways. For example, in some series, images differ in spatial position. In other series, images differ in projection, for example AP or Left Lateral views in radiography. In other series, images differ temporally, for example where they fall within the cardiac cycle, as in echocardiography, cardiac MRI or cardiac nuclear medicine scans. In other series, images may differ in other ways and the systems and methods discussed herein may be used to select matching images in different series based on the particular characteristics of selected image series.

Figure 12:
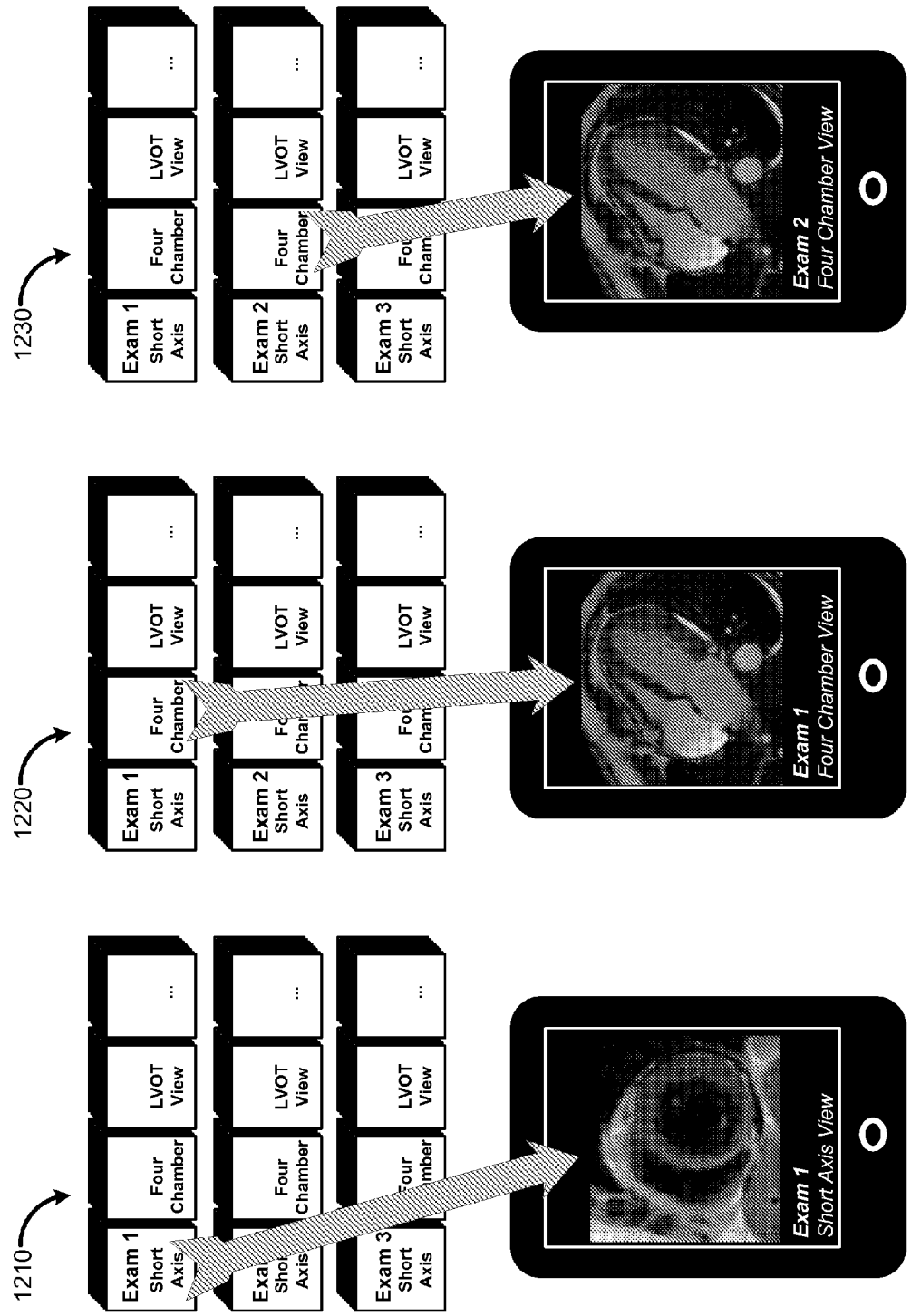
FIG. 12 illustrates three exams, each having multiple image series that include images differing temporally, such as cardiac MRI images where images within each series are in the same spatial location and plane but differ temporally, e.g. where they fall within the cardiac cycle.

FIG. 12 illustrates three exams, each having multiple image series that include images differing temporally, such as cardiac MRI images where images within each series are in the same spatial location and plane but differ temporally, e.g. where they fall within the cardiac cycle. Columns 1210, 1220, 1230 each include the same three exams and image series within the exams, but illustrate different images within the exams being selected for display on the illustrated computing devices. The computing device displaying cardiac images could be any of a number of different computing devices, including handheld devices or scanners, such as an ultrasound scanner.

When users view series from exams such as cardiac MRI, ultrasound, or nuclear medicine studies, series may be viewed in cine mode, where images within the series are automatically displayed serially in a loop, for example at a rate of 20 images/second. This allows the user to view cardiac motion. Alternatively, images can be viewed in a static mode, where an image within the series is displayed until the system receives user input to change it. Static viewing of images will be described first with respect to FIG. 12 followed by a description of cine viewing.

When viewing images in static mode, the user can provide input at any time to change the image within the displayed series, as described in other embodiments. In column 1210, an image of exam 1 from a Short Axis View series is displayed at a certain point in the cardiac cycle.

In column 1220, the user has provided input associated with a command to display a different series within the same exam, in this example, a four chamber view. In response to receiving the command to change from the short axis view to the four chamber view, the computing device automatically selects an image from the four chamber view series that matches the temporal position of the image currently displayed.

In column 1230, the user has provided input associated with a command to display an image from a different exam. Based on system and methods described herein, the series from the new exam that matches the orientation and plane of the current exam is automatically chosen. In addition, in this embodiment an image from the new series is automatically chosen that matches the temporal position of the image currently displayed. Thus, as shown in column 1230, an image from the four chamber view of exam 2 is selected for display in response to an exam change command received while viewing an image of the four chamber view of exam 1.

When viewing images in cine mode, the user can provide input at any time to change the series or exam, as described in other embodiments. In column 1210, an image from the Short Axis View is displayed.

In column 1220, the user has provided input to display a different series within the same exam, in this example, a four chamber view. When a new series is displayed, it may also be displayed in cine mode. Thus, when the change series command has been received, with images of the short axis view being displayed in cine mode, the computing device automatically selects images of the four chamber view of the same exam for display in cine mode.

In column 1230, the user has provided input to display a different exam. Based on system and methods described herein, the series from the new exam that matches the orientation and plane of the series displayed in the current exam is automatically chosen, and the images from the selected series are displayed in cine mode. In one embodiment, when in cine mode, images of different series and/or exams are selected and played in cine mode at the same speed as the previous image series such that the user can switch between series and/or exams with the cine motion continuing in an undelayed manner.

Figure 13:
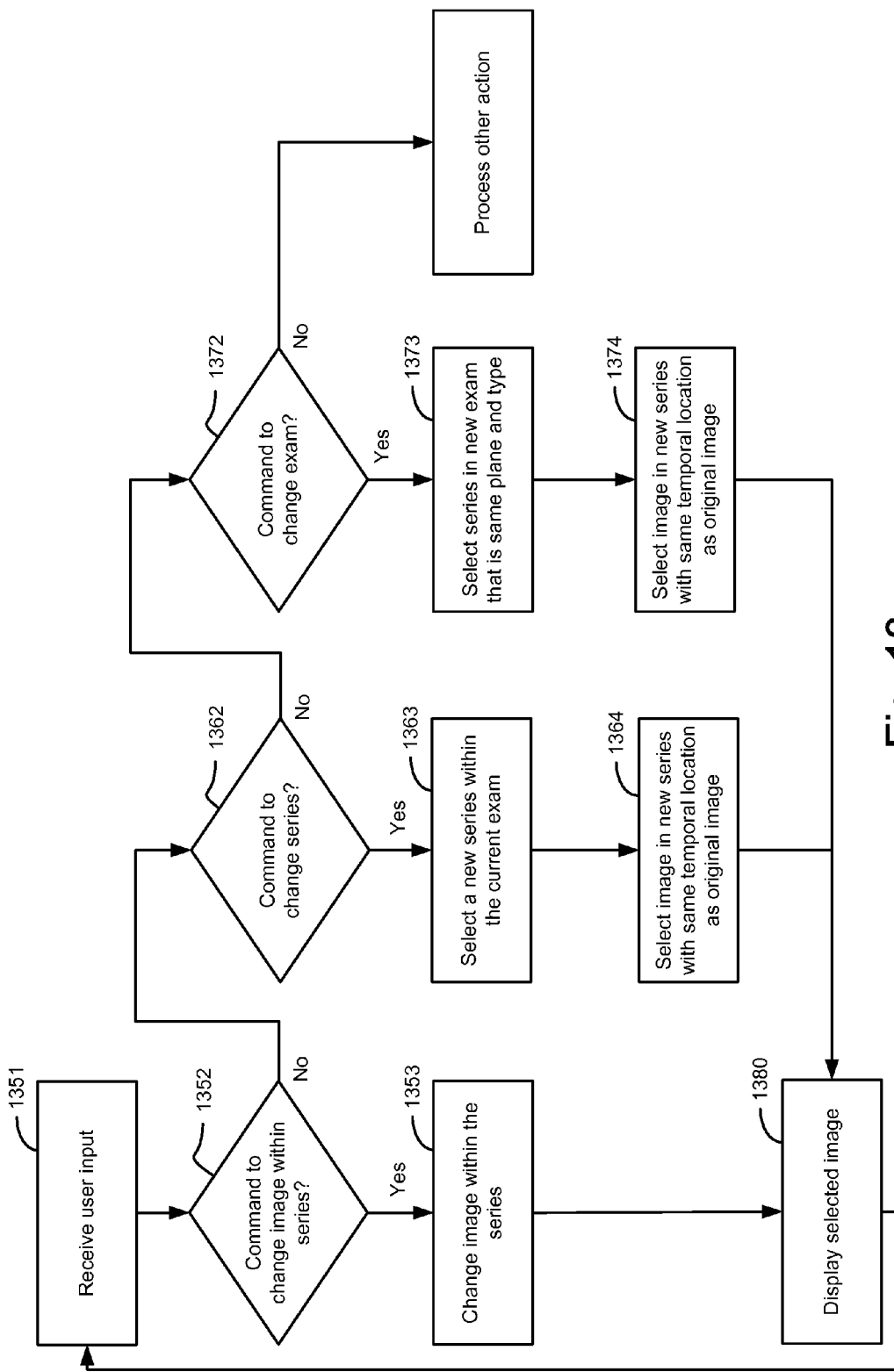
FIG. 13 is a flowchart illustrating one embodiment of a method of navigating between image series having images that vary temporally.

FIG. 13 is a flowchart illustrating one embodiment of a method of navigating between image series having images that vary temporally. Depending on the embodiment, the method of FIG. 13 may include fewer or additional blocks and/or the blocks may be performed in a different order than is illustrated. Software code configured for execution on a computing device in order to perform the method of FIG. 13 may be provided on a computer readable medium, such as a compact disc, digital video disc, flash drive, hard drive, memory device or any other tangible medium. Such software code may be stored, partially or fully, on a memory of a computing device, such as the computing devices 150, 250, and/or other computing devices illustrated in the Figures, in order to perform the method outlined in FIG. 13 by those respective devices. For ease of explanation, the method will be described herein as performed by a computing device, which should be interpreted to include any one or more of the computing devices noted above and/or any other suitable computing device.

The method of FIG. 13 is similar to the method of FIG. 8 in that user input is received in block 1351, and a series of checks are performed in order to determine a command that is indicated by the user input. In FIG. 13, at block 1352 the computing device determines whether a command to change images within a current series has been received, at block 1362 the computing device determines whether a command to change series has been received, and at block 1372, the computing device determines whether a command to change exams has been received. As noted with reference to FIG. 8, these decisions blocks 1352, 1362, 1372 may be performed in a different order than is illustrated, or may be performed concurrently.

If a command to change images within a current series is received in block 1352, the method continues to block 1353 where another image within the current series is selected for display. The method then moves to block 1380 where the selected image is displayed, and then returns to block 1351 where additional user input may be received.

If a command to change series is received in block 1362, the method continues to block 1363 where a new series within the current exam is selected. The method then continues to block 1364 where an image within the selected new series having the same (or similar) temporal location as the current image is selected. The method then continues to block 1380 where the selected image is displayed and then to block 1351 where further user input may be received.

If a command to change exams is received in block 1372, the method continues to block 1373 where a series within a new exam is selected. In one embodiment, the newly selected exam includes a same series type as the current exam. Thus, the series of the new exam that is selected is the same series type as is currently displayed in the current exam. In an embodiment where the newly selected exam does not include a same series type as the current exam, a similar series type in the newly selected exam may be selected, such as by using associations between series types as discussed above with reference to FIG. 11. Once a series within the new exam is selected in block 1373, the method continues to block 1374 where the computing device selects an image in the selected series with the same (or similar) temporal location as the currently displayed image. The method then continues to block 1380 where the selected image is displayed and then to block 1351 for further user input may be received.

Viewing Exams with Multiple Views

Figure 14:
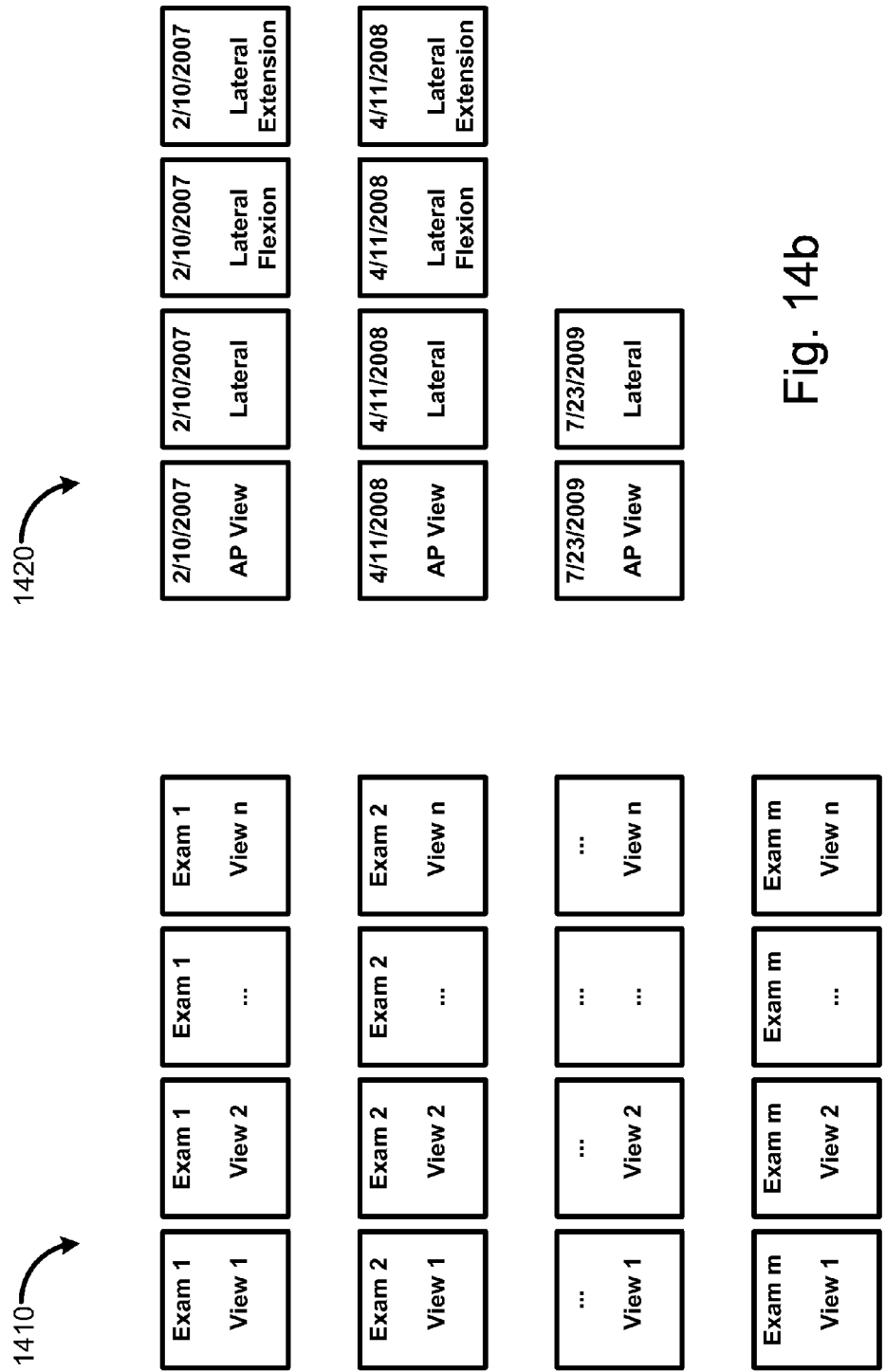
FIGS. 14a and 14b illustrate multiple exams each having multiple views within the exams.

FIGS. 14a and 14b illustrate multiple exams each having multiple views within the exams. In particular, FIG. 14a illustrates exams 1-m that each include multiple views for each of the exams. Similarly, FIG. 14b illustrates three exams (a first exam dated Feb. 10, 2007, a second exam dated Apr. 11, 2008, and a third exam dated Jul. 23, 2009), each having multiple views (e.g., AP view, lateral view, and lateral flexion and lateral extension views in the first two exams).

"Views" may include different projections in a Computed Radiography or Mammography exam, for example. Views may be produced with various methods and various imaging modalities. For example, in the case of radiography, views may represent projections, such as AP (anterior-posterior) and Left Lateral. In the case of 3D Volume rendering, views may be created and stored or created dynamically, e.g. an anterior view, posterior view, and lateral view. In one embodiment, views are created and stored prior to the point where the user displays them, with each block in FIGS. 14a and 14b representing a series of stored images. Thus, in the embodiment of FIGS. 14a and 14b, each series may contain a single image. In other embodiments, views may include more than one image.

In other embodiments, the "views" depicted within the blocks represent parameters that describe how a view is to be created, but the actual image is created dynamically at the time it is to be displayed. For example, in the case of 3D volume rendering the various views may represent parameters such as the view angle, magnification, and other rendering parameters that allow the views to be created dynamically for display in response to user interaction.

In other embodiments, exams may comprise a mixture, where some views represent stored images and other views represent rendering parameters that may be stored based on site or user preferences or created dynamically based on the stored views in other exams. For example, one exam might comprise views from cervical spine radiographs. Another exam might be an MRI of the cervical spine. Another exam might be a high resolution CT. As an example, the lateral view of the cervical spine, a stored imaged, might be matched with the midline sagittal view from the cervical spine MRI. These views might be matched with a midline sagittal MPR image dynamically reconstructed from the cervical spine CT.

In response to user input, the computing device displaying an image of a particular exam may be instructed to display another image within the same exam or an image within a different exam. For example, a first user input (e.g., a finger swipe from left to right) may be associated with a change image command that causes the computing device to select another image within the same exam for display (e.g., an adjacent view to the currently displayed view). In this example, a second user input (e.g., a finger swipe from up to down) may be associated with a change exam command that causes the computing device to select an image from another exam that corresponds to the current image (e.g., view 1 of exam 1 may be replaced with view 1 of exam 2).

FIG. 14b illustrates three exams, each comprising radiographs of the cervical spine. The exam dated Jul. 23, 2009 has two views whereas the other exams, dated Feb. 10, 2007 and Apr. 11, 2008 each have four views. In this embodiment, it is possible for a user to request display of a view that does not exist. For example, if a change exam command is received while the Lateral Flexion view from Apr. 11, 2008 is displayed, where the requested new exam is the Jul. 23, 2009 exam, no similar view exists. Thus, in one embodiment the computing device may display an indicator that a similar view does not exist in that exam. In other embodiments, the closest similar view may be displayed, for example the lateral view, possibly along with an indication that an exact match was not found.

Figure 15:
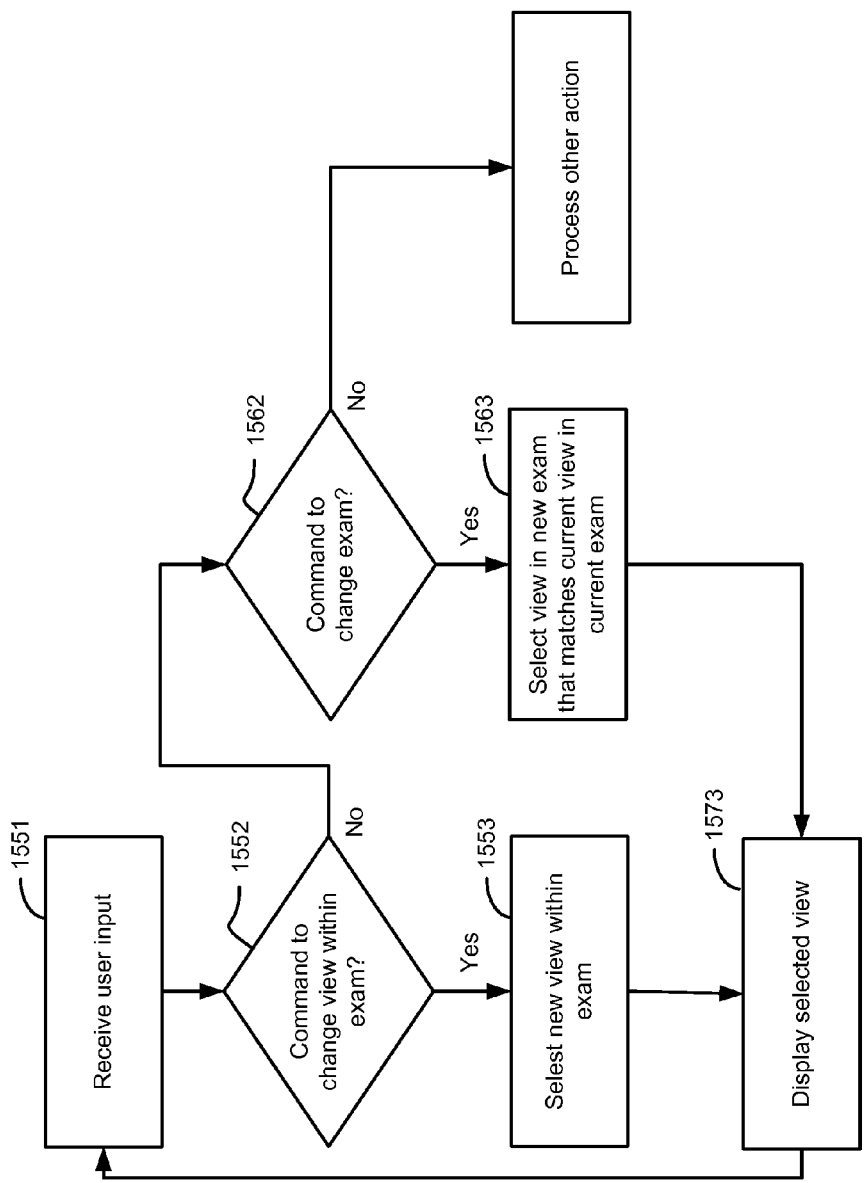
FIG. 15 is a flowchart illustrating one embodiment of a method of navigating between views, where stored views comprise images that may be selectively displayed in response to user input.

FIG. 15 is a flowchart illustrating one embodiment of a method of navigating between views, where stored views comprise images that may be selectively displayed in response to user input. Depending on the embodiment, the method of FIG. 15 may include fewer or additional blocks and/or the blocks may be performed in a different order than is illustrated. Software code configured for execution on a computing device in order to perform the method of FIG. 15 may be provided on a tangible computer readable medium, such as a compact disc, digital video disc, flash drive, hard drive, memory device or any other tangible medium. Such software code may be stored, partially or fully, on a memory of a computing device, such as the computing devices 150, 250, and/or other computing devices illustrated in the Figures, in order to perform the method outlined in FIG. 15 by those respective devices. For ease of explanation, the method will be described herein as performed by a computing device, which should be interpreted to include any one or more of the computing devices noted above and/or any other suitable computing device.

The method of FIG. 15 is similar to the method of FIG. 8 in that user input is received in block 1551, and a series of checks are performed in order to determine a command that is indicated by the user input. In FIG. 15, at block 1552, the computing device determines whether a command to change views within a currently selected exam has been received, and at block 1562 the computing device determines whether a command to change exams has been received. As noted above, these blocks may be performed in a different order than is illustrated, or may be performed concurrently.

If a command to change views within a current exam is received in block 1552, the method continues to block 1553 where a new view within the current exam is selected. If a command to change exams is received in block 1562, the method continues to block 1563 where a view in a new exam that matches the current view in the current exam is identified and selected. The method then continues to block 1573 where the computing device displays the selected view, and then returns to block 1551 where additional commands may be received.

Figure 16:
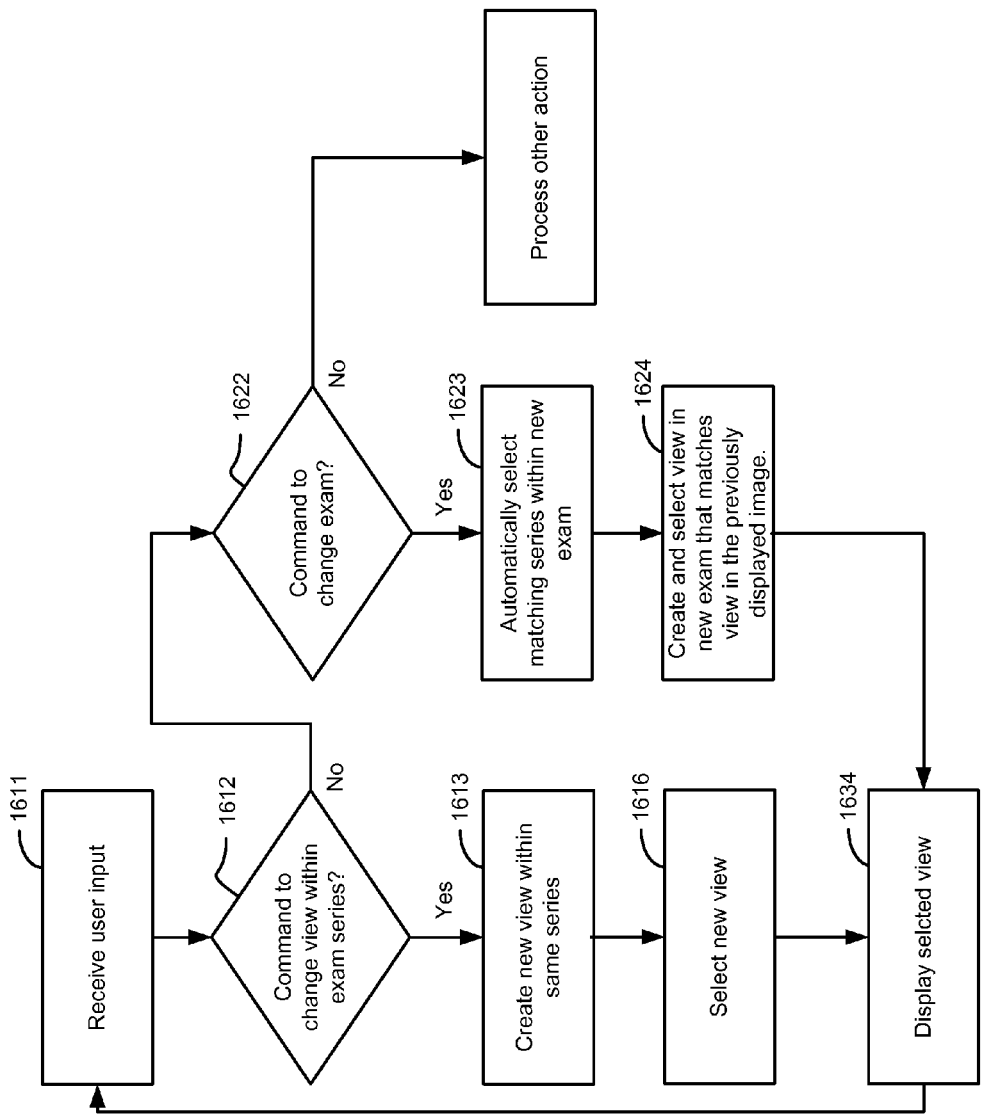
FIG. 16 is a flowchart illustrating one embodiment of a method of navigating between views, where the stored views comprise rendering parameters that that are sufficient to create views, for example with 3D volume rendering, MPR or MIP.

FIG. 16 is a flowchart illustrating one embodiment of a method of navigating between views, where the stored views comprise rendering parameters that that are sufficient to create views, for example with 3D volume rendering, MPR or MIP. Depending on the embodiment, the method of FIG. 16 may include fewer or additional blocks and/or the blocks may be performed in a different order than is illustrated. Software code configured for execution on a computing device in order to perform the method of FIG. 16 may be provided on a tangible computer readable medium, such as a compact disc, digital video disc, flash drive, hard drive, memory device or any other tangible medium. Such software code may be stored, partially or fully, on a memory of a computing device, such as the computing devices 150, 250, and/or other computing devices illustrated in the Figures, in order to perform the method outlined in FIG. 16 by those respective devices. For ease of explanation, the method will be described herein as performed by a computing device, which should be interpreted to include any one or more of the computing devices noted above and/or any other suitable computing device.

The method of FIG. 16 is similar to the method of FIG. 8 in that user input is received in block 1611, and a series of checks are performed in order to determine a command that is indicated by the user input. In FIG. 16, at block 1612, the computing device determines whether a command to change views within a currently selected exam series has been received, and at block 1622 the computing device determines whether a command to change exams has been received. As noted above, these blocks may be performed in a different order than is illustrated, or may be performed concurrently.

If a command to change views within a current exam series is received in block 1612, the method continues to block 1613 where the computing device creates a new view within the same series, such as via 3D volume rendering, MPR or MIP. The method then continues to block 1316 where the new view is selected for display. If a command to change exams has been received at block 1622, the method continues to block 1623 where the computing device automatically selects a matching series within a different exam. The method then continues to block 1624 where the computing device creates and selects a view in the new exam that matches the currently displayed view. After a new view is selected in block 1616 or 1624, the method continues to block 1634 where the computing device displays the selected view, and then returns to block 1611 where additional commands may be received.

In one embodiment, the matching series within the new exam described above is a second series in the same exam. Therefore the system above would allow a user to create a view from one series, in this example a volumetric acquisition, and then on changing to a second series in the same exam, also a volumetric acquisition in this example, be automatically presented with a similar view.

Figure 17:
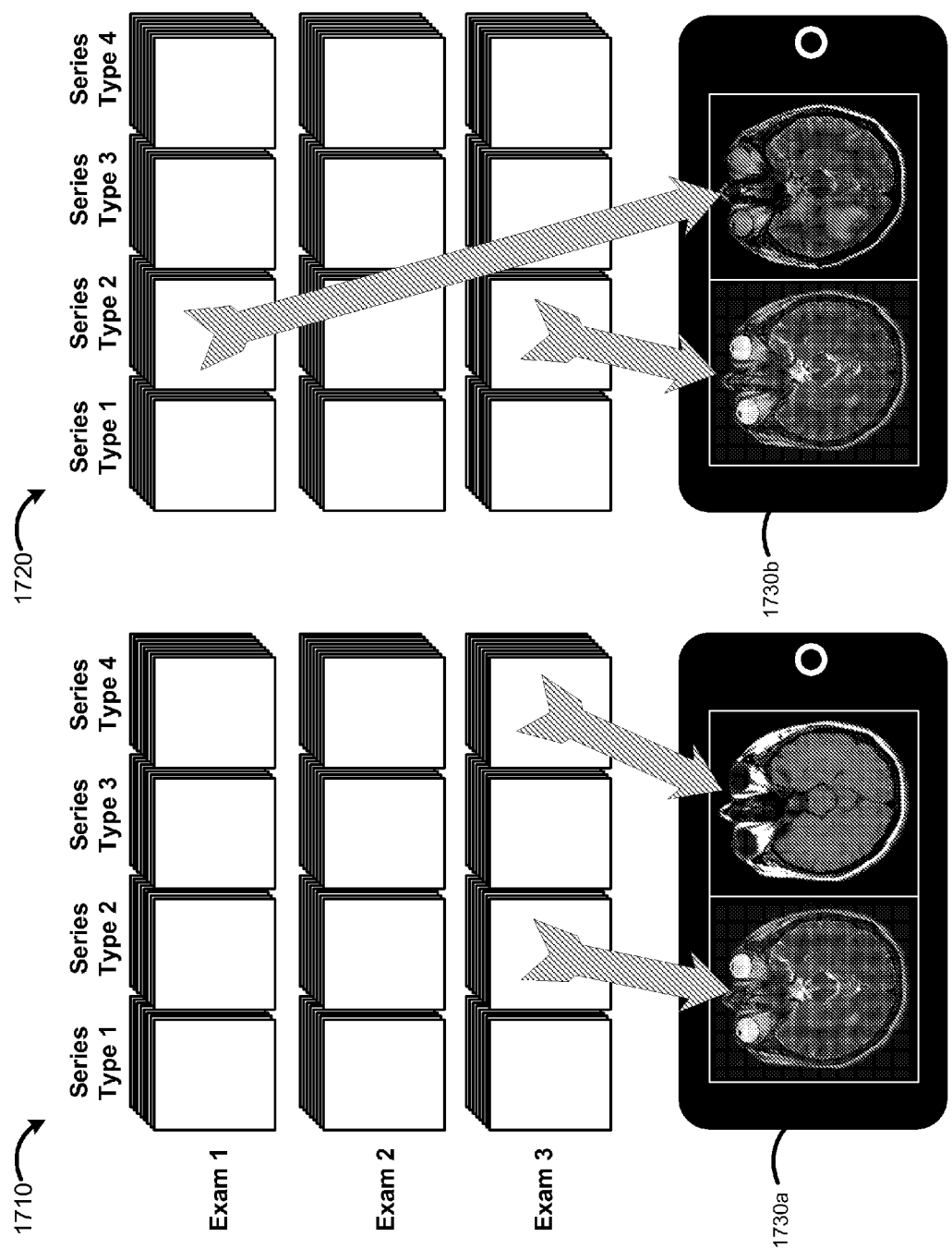
FIG. 17 is a diagram illustrating navigation between images of exams each having multiple series types using a display device that is capable of depicting multiple images concurrently.

FIG. 17 is a diagram illustrating navigation between images of exams each having multiple series types using a display device 1730 that is capable of depicting multiple images concurrently. In this embodiment, more than one image may be displayed simultaneously on the computing device and the computing device may automatically select one or both of these images. Computing device 1730 is shown at two different times, 1730a and 1730b. View 1710 is an example where there are three exams, each consisting of four series. In the example illustrated, the images are brain MRI images and each series consists of images at different spatial positions.

In the example of computing device 1730a, the two images displayed are from Exam 3. In particular, the left image is from Series Type 2 (an Axial T2 series in this example) and the right image is from Series Type 4 (an Axial T1 weighted series in this example).

The user can provide input to the computing device, for example using the gestures illustrated in FIG. 7, to change the image displayed within a series, the series displayed within an exam, or the exam displayed. For example, when a user provides input to change one of the series displayed within an exam, the new series is displayed. Based on systems and methods described herein, if the new series can be matched to the series displayed in the other frame of the computing device, for example because it is in the same plane, then the image chosen to display in the new series will be automatically chosen to match the spatial location of the image displayed in the other frame. The images on computing device 1730b are those selected by the computing device in response to the user requesting a change in exams for the right image displayed on computing device 1730a (such as by providing a finger swipe or other input on the right image). In response to the requested change in exam command for the image in the right frame, the computing device 1730 selects an image from another exam (exam 1 in this example) that most closely matches the spatial position and/or series type of the image displayed in the left frame, resulting in display of an image from Series Type 2 of Exam 1 in the right frame of device 1730b.

Figure 18A:
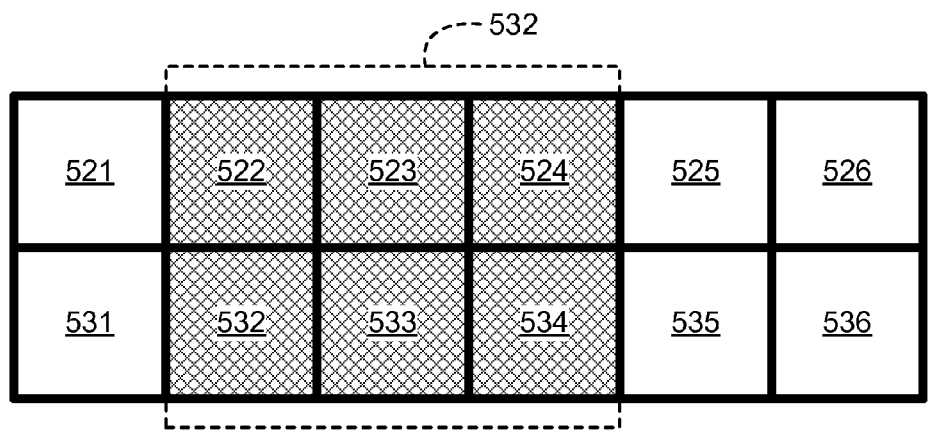
FIG. 18a depicts a first group of images and/or series and FIG. 18b depicts a second group of images and/or series.
Figure 18B:
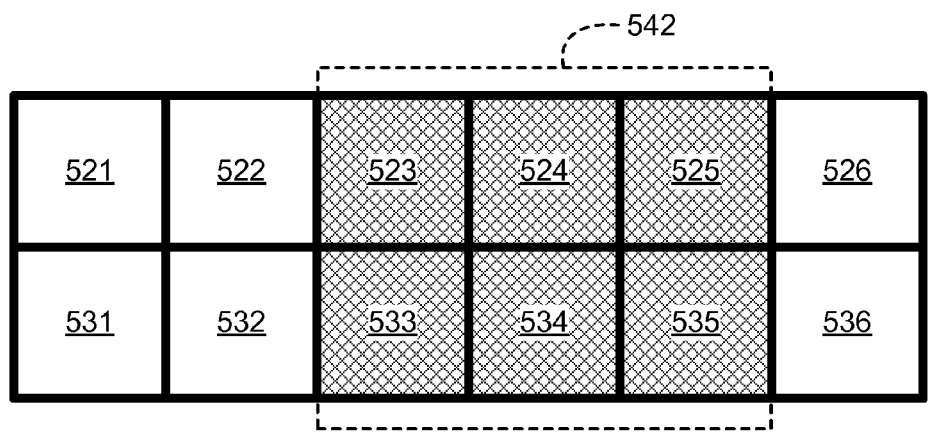

FIGS. 18a and 18b are block diagrams illustrating conceptually how multiple images of an exam and/or series with multiple images within exams may be selectively viewed. In this embodiment, blocks 521-526 may represent different image series of a first exam, while blocks 531-536 may represent different image series of a second exam. In the example shown, a computing device is configured to display six images concurrently, such as images in the group 532. In other embodiments, the number of exams, series, and/or images that can be concurrently displayed on a computing device varies.

FIG. 18a depicts a first group 532 of images and/or series and FIG. 18b depicts a second group 542 of images and/or series. The change in images displayed between FIGS. 18a and 18b may be caused by any predefined user input, such as a finger swipe to the right on the display device, a mouse command, voice command, or command provided in any other manner.

Figure 19A:
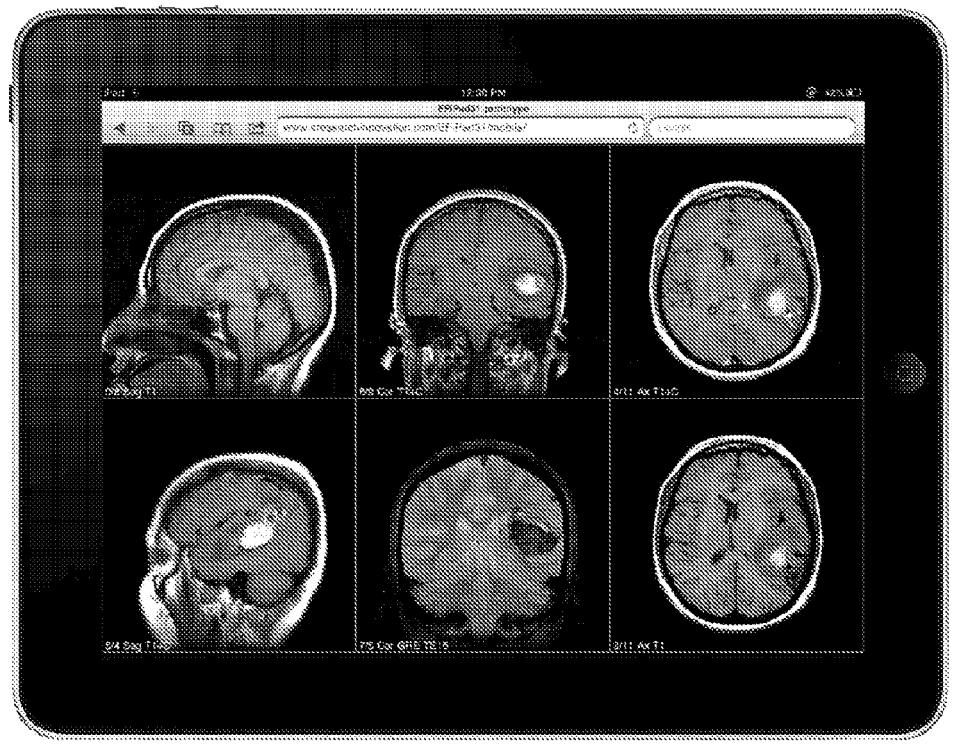
Figure 19B:
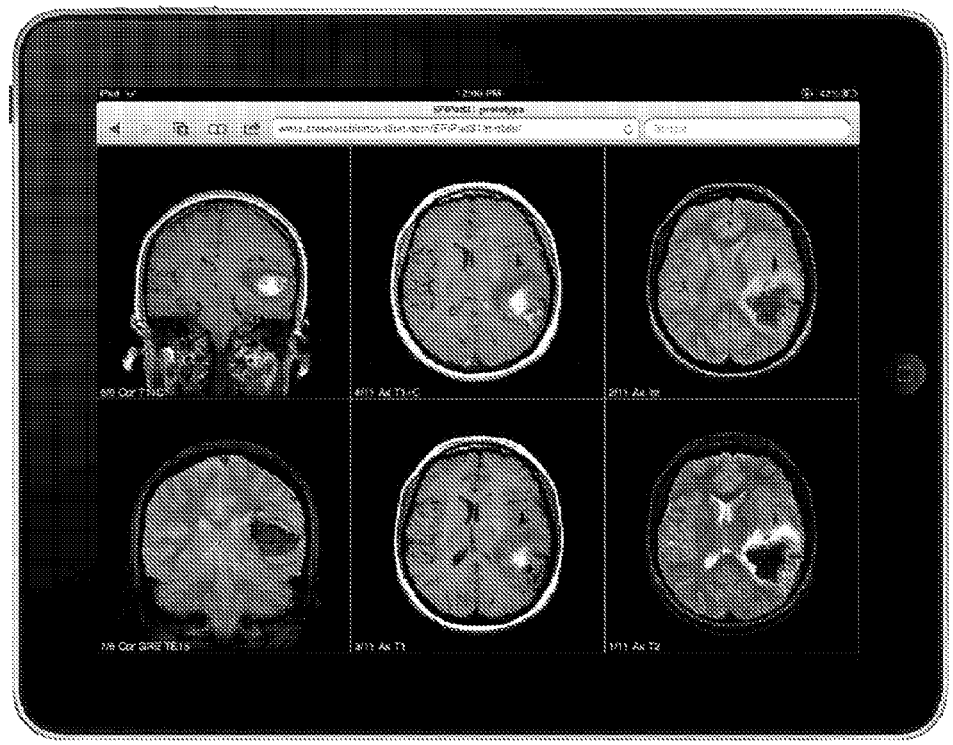
FIG. 19b depicts a computing device displaying images of a second group of series (e.g., as shown in FIG. 18b).

FIG. 19a depicts a computing device displaying images of the series in first group 532 (e.g., as shown in FIG. 18a), while FIG. 19b depicts a computing device displaying images of the series in the second group 542 (e.g., as shown in FIG. 18b). In the embodiment of FIG. 19, the images are from a brain MRI, with each frame displaying an image from a different series.

Based on user input, for example a swipe motion on the touchscreen of the tablet computer illustrated in FIG. 19, the series selected for display may be changed in certain embodiments. For example, left and right swipes on the touchscreen may change the group of series displayed, as depicted FIG. 18. As noted above, FIG. 18b shows the series displayed in response to a left finger swipe on the computing device displaying images from the series of group 532 (FIG. 18a). Note that group 532 includes the series depicted by blocks 522 and 532 while blocks 522 and 532 are no longer displayed in response to command to change the series that are displayed to those depicted in group 542. In a similar manner, the user can provide the same command again in order to cause series depicted by blocks 523 and 533 to no longer be display and to add the series depicted by blocks 526 and 536 to the display.

Based on systems and methods described herein the particular images displayed within the newly displayed series may be automatically chosen based on images displayed in the series that remain displayed after the user input.

Note that the images displayed in the right two frames of FIG. 19a, corresponding to blocks 524 and 534 in FIG. 18a, are axial images from the exam. After user input, these series have been moved to the middle column as depicted in FIG. 19b. Newly displayed series are displayed in the right column. In one embodiment the image selected for display within the newly displayed series is chosen to match the spatial position of the adjacent series, in this example the series in the middle column, if the series is in a similar plane, e.g., axial. In another embodiment, the newly displayed series are automatically selected from the undisplayed series so that they are in the same plane as the adjacent series, in this case axial, and the images within series are automatically selected to match as closely as possible the spatial position within the adjacent series, in this example the series displayed in the middle column. While the series used for illustration in FIG. 19 are from a single exam, in other embodiments series may come from two or more exams.

Figure 20:
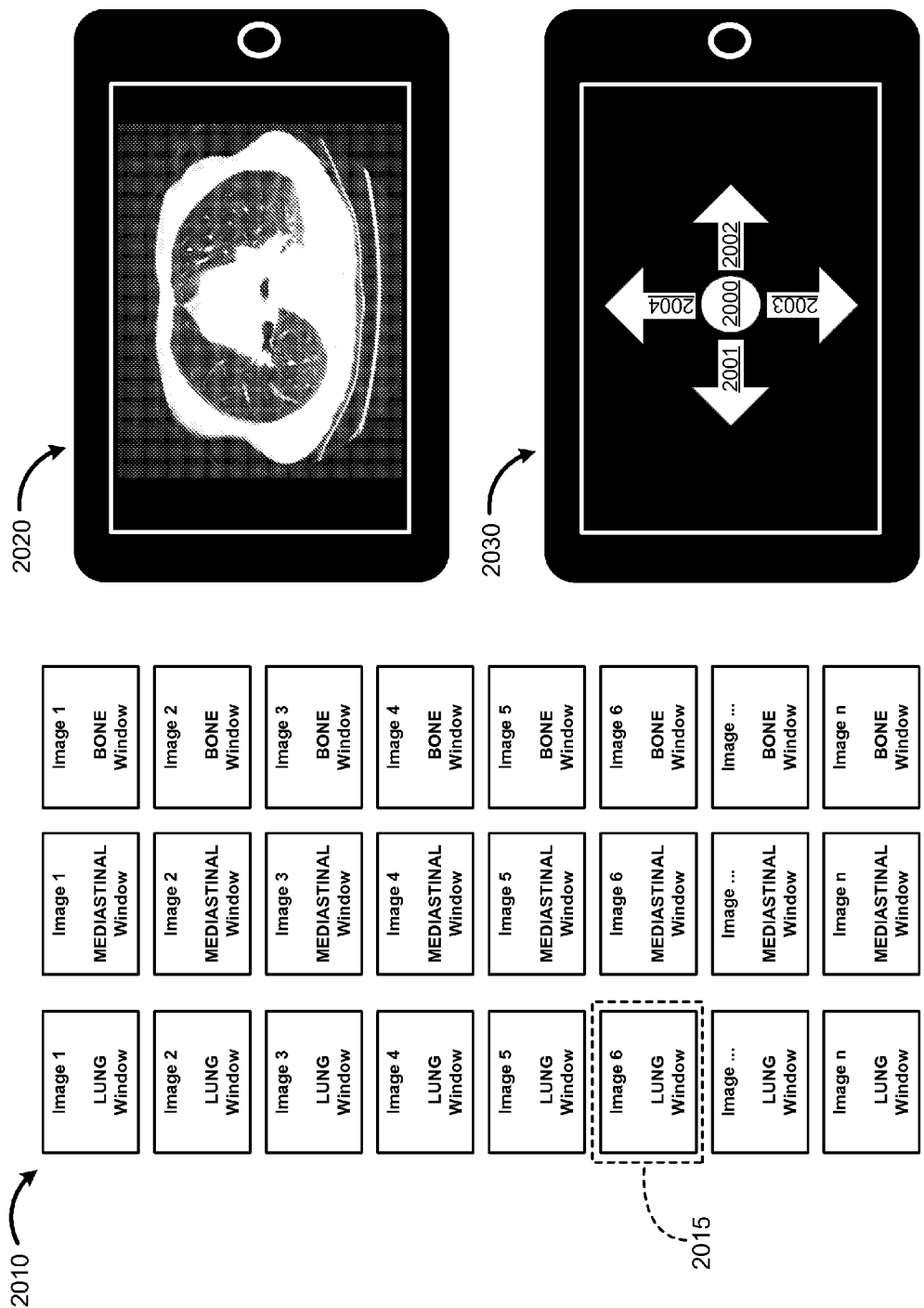
FIG. 20 illustrates a series of images that are numbered 1 to n that are selectable for display using a variety of pre-set display parameters.

FIG. 20 illustrates a series of images 2010 that are numbered 1 to n that are selectable for display using a variety of pre-set display parameters. In the example shown, display parameters comprising "Lung windows", "Mediastinal windows", and "Bone windows", are included as example display parameters that may be available for display of the various images. A computing device 2020 is illustrated displaying an example image from a chest CT exam (image 6 of the example image series 2010). In the example shown, a lung window display parameter is applied to image 6, which corresponds to block 2015 of the image series 2010.

View 2030 shows a computing device with arrows on the screen depicting input gestures that a user could employ on a touch screen, such as computing device 2020. Specifically, the user might touch any region of the screen, depicted as region 2000, and move his finger up, down, left or right, represented by arrows 2004, 2003, 2001 and 2002 in order to initiate the following changes to the image displayed and/or parameters for display of the image:

Up gesture: decrease the number of the image displayed, e.g. from 6 to 5.
Down gesture: increase the number of the image displayed, e.g. from 6 to 7.
Right gesture: change the display preset by selecting the next one in a stored list, e.g., from lung window to mediastinal window.
Left gesture: change the display preset by selecting the prior one in a stored list, e.g., from bone window to mediastinal window.

Thus, in this embodiment, images can be selected with a first type of user input (e.g., up/down gestures) and display settings for the images can be adjusted with another type of user input (e.g., left/right gestures). Accordingly, a user can easily change display setting among a series of preset display settings and then move to a new image while retaining the latest display settings.

As with other embodiments discussed herein, the actual user inputs (e.g., up/down and left/right movements) provided are only examples of inputs that could be used to cause the indicated action (e.g., change in the image displayed). Any other inputs, provided in any available manner, may also be used in place of the indicated example user inputs.

Figure 21:
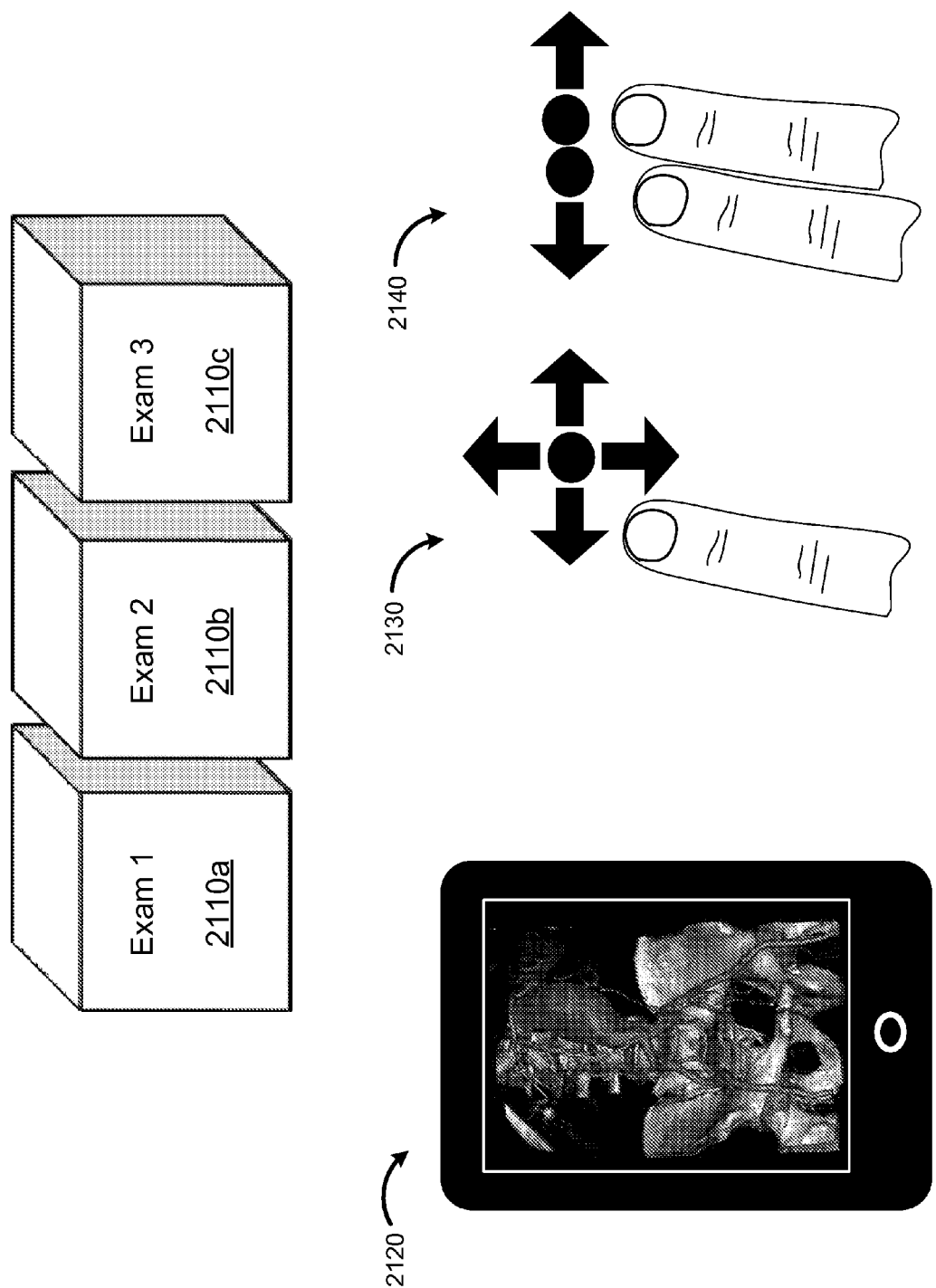
FIG. 21 illustrates multiple 3D volumetric series.

FIG. 21 illustrates multiple 3D volumetric series 2110a, 2110b, and 2110c. In this embodiment, a user of the computing device 2120 may navigate between images generated from the various volumetric series using the gestures indicated in views 2130 and 2140, for example. In other embodiments, any other number of 3D imaging volumes may be similarly navigated using any other input commands. Depending on the embodiment, the imaging volumes may come from a single exam or multiple exams and may be from the same or different modalities (on the same or different dates). For example, the exams could be CTA exams of the abdomen used to assess changes over time of an abdominal aortic aneurysm. In addition, the series could be 4-dimensional series, e.g. a 3D beating heart for example from MRI or cardiac ultrasound. If images are played in cine mode then the displayed series could be played as a cine loop. Changing to another 4D volume may use the same volume rendering technique and view angle.

As noted above, various techniques can be used to create images from 3D volumetric exams, including volume rendering (VR), surface rendering, multiplanar reformatting (MPR), and Maximum Intensity Projection (MIP).

In order for the user to look for changes, for example in an abdominal aortic aneurysm, it may be helpful to use the same technique to render the volumetric information for an exam and prior comparison exams. In addition it may be helpful to compare like projections. In one embodiment, when the user switches viewing between exams, the same rendering technique and view angle are utilized to display the information.

For example, computing device 2120 is shown illustrating a volume rendering of an abdominal CTA in a patient with an abdominal aortic aneurysm. When the user switches between volumes, for example from exam 1 to exam 2 (e.g., exams obtained at different times), the same rendering technique and view angle may be automatically utilized by the computing device 2120 in generating an image from exam 2 for display.

View 2130 illustrates example gestures that could be used to provide user input on the computing device 2120. Such up-down and left-right motions could be utilized to alter the viewing angle of the rendered volume.

View 2140 illustrates example gestures that the user might use to change to a different exam. For example, two finger swipes to the left might result in display of an exam performed before the current exam and a swipe to the right might result in display of an exam performed after the current exam. As noted above, the currently selected viewing angle of an image may be automatically selected for use in generating an image from a newly selected exam, such that the user can compare like images from the different exams.

In other embodiments, other techniques may be used, such as multiplanar reformation (MPR). For example, the user could choose the plane of reconstruction for a volume as well as other rendering parameters such as slice thickness, window width, and window level. Switching to other volumes may result in creation of an MRP reformation at the same anatomic position and use the same rendering parameters.

Navigation of Other Information Types

Figure 22:
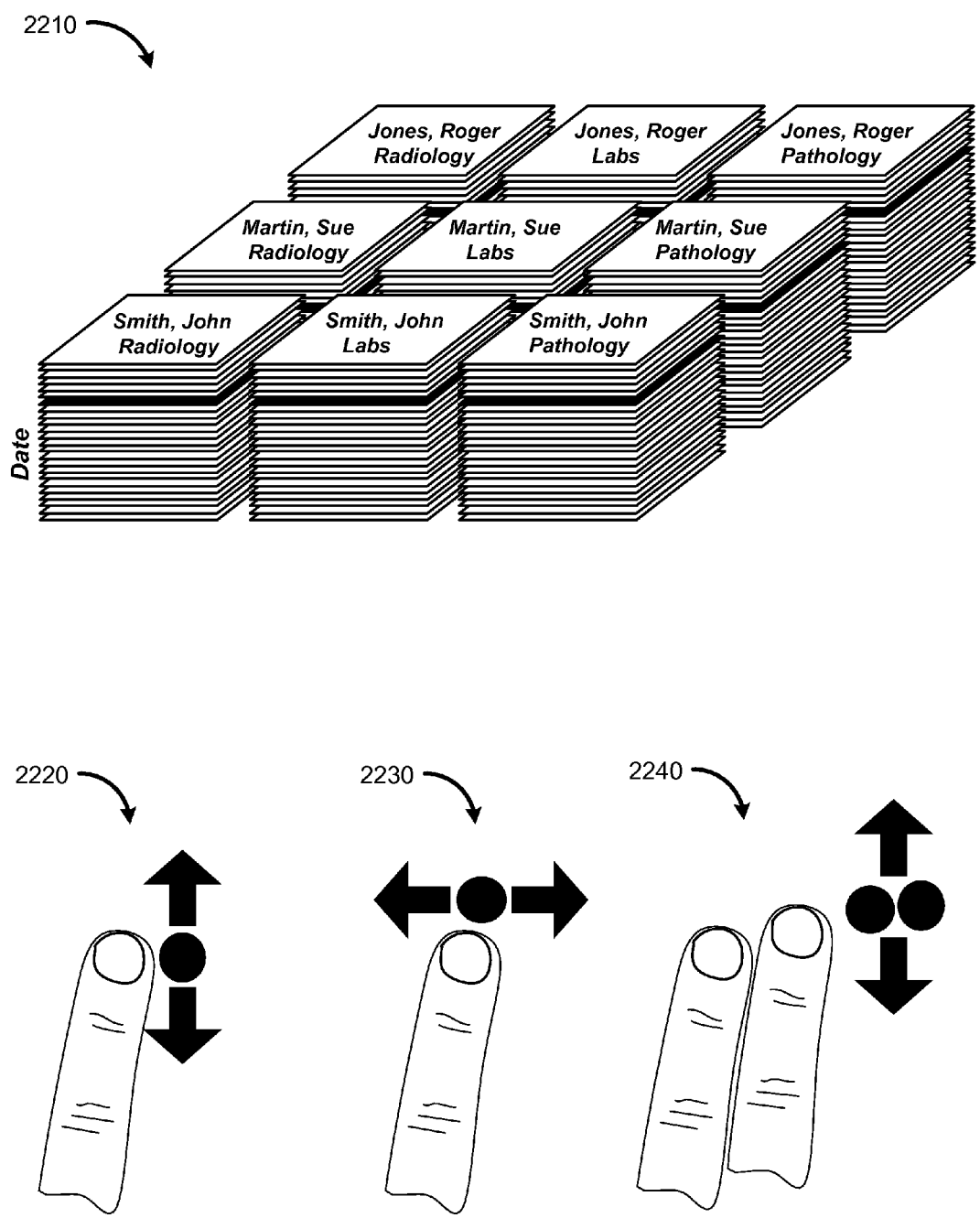
FIG. 22 illustrates nine stacks of "documents," where each stack represents a category of information for a patient.

FIG. 22 illustrates nine stacks of "documents" 2210, where each stack represents a category of information for a patient. In this embodiment, each row of stacks is associated with a different patient and each column of stacks is associated with a different category of information (e.g., radiology, labs, pathology, etc.). In this embodiment, layers within each stack may be navigated based on time. In one embodiment, layers within stacks represent portions of information from documents, or associated with documents, such as dates of exams/reports or individual values/entries on a document, such as individual values in a lab report, for example.

In the embodiment of FIG. 22, the stack in the upper left represents radiology exams for patient Roger Jones. Each layer of the stack may represent a different exam, for example radiology exams performed at different times. The information represented by each layer, and available for presentation to the user, may be, for example, a text report, numerical information, images, a graphic, notes, labs, reports (e.g., radiology, pathology, etc.), or any combination of these and/or other related information. In one embodiment, information in the documents 2210 may be accessible by an electronic medical record (EMR) system. In one embodiment, information represented by the various layers may be stored in a database or other data structure.

View 2220 illustrates a gesture that may be used on a touchscreen to change patients, staying within the same category of information, such as moving between rows of stacks (with reference to stacks 2210). In different embodiments, the exam within the category may also change. In one embodiment, when switching to a different stack, the default is to display the appropriate category of information from the oldest exam that has not been displayed to the user. In another embodiment, the newest exam is displayed.

View 2230 illustrates a gesture that may be used on a touchscreen to change categories of information displayed for a same patient, such as by moving between columns within a current row (with reference to stacks 2210).

View 2240 illustrates a gesture that may be used on a touchscreen to change documents in a current stack, such as between documents associated with a specific category for a specific patient. With reference to stacks 2210, the gesture of view 2240 may navigate up and down, respectively, between items in a currently selected stack to navigate to documents having different dates/times. For example, two-finger swipe down could be used to display information from the next older exam and two-finger swipe up could be used to display information from the next newer exam.

Figure 23:
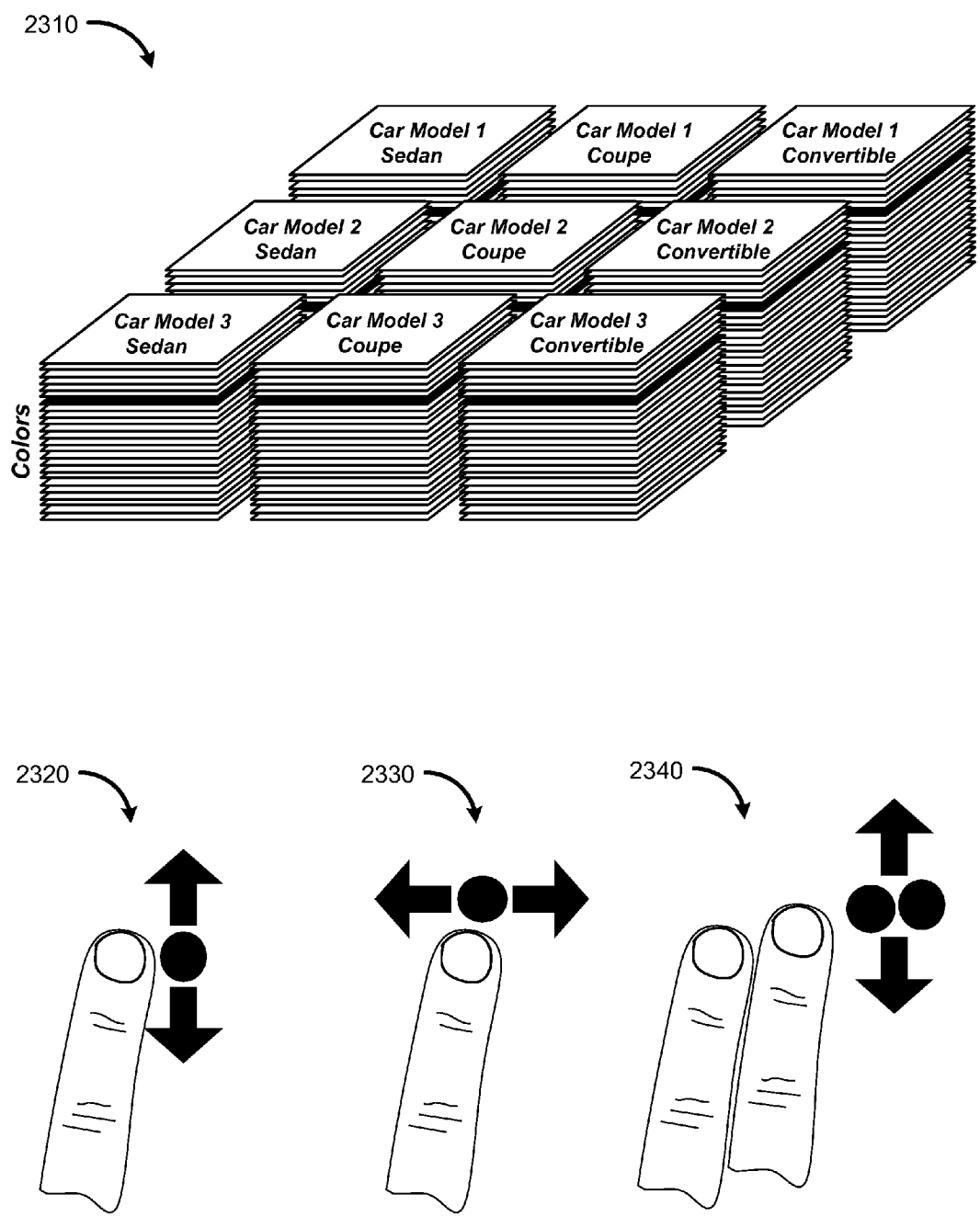
FIG. 23 illustrates nine stacks of data structures, each comprising multiple layers.

FIG. 23 illustrates nine stacks of data structures 2310, each comprising multiple layers. In this embodiment, each stack represents a configuration of a particular automobile. For example, the information contained within each stack may comprise one or more of text, numerical information, graphical information, images, videos, sound recordings, or other any information associated with the respective automobile. In this exemplary embodiment related to cars, each row of stacks is associated with a different car model and each column of stacks is associated with a different configuration of automobile (e.g., sedan, coupe, convertible, etc.), and the layers in a particular stack related to different data collections that comprise colors of automobiles. In the embodiment of FIG. 23, the stack in the upper left represents car model 1 sedan, and the data collections in that stack relate to different colors of that model and configuration of automobile.

In this embodiment, the gestures illustrated in views 2320, 2330 and 2340 may be used to change car models, configurations of car models, and colors, respectively with a computing system that employs a touch screen (or by using corresponding inputs from another computing device, such as mouse movements on a desktop computer). For example, up or down swipes may be used to change car models, keeping configuration and color constant. Thus, in one embodiment, a computing device may be configured to update an image of an automobile (e.g., a stock image and/or image of a particular automobile for sale or rent) and/or data regarding the automobile in response to user inputs on the touchscreen and according to the relationships defined by the data structures 2310.

In one embodiment, the example system illustrated could be used to configure a new car that would be built. In another embodiment, the example system could be used to view information on and select used cars from an inventory maintained in a database or other data structure.

In other embodiments, the type of information varies, such as to include information regarding different products, in order to implement an e-commerce system.

FIG. 24 illustrates an example user interface 2410 that may be generated and updated using navigation techniques discussed with reference to FIG. 23. For example, the user interface 2410 illustrates the 3 dimensions discussed with reference to FIG. 23, namely, model, configuration, and color. In other embodiments, any other type of information could be represented.

In one embodiment, price may be added as a fourth dimension and may be navigated using systems and methods describe herein. For example, view 2420 illustrates a two-finger gesture that a user might use to navigate to the next or prior car in the same price category, where model, configuration and/or color may vary. The pinch gesture illustrated in view 2430 may be used to change the price category, where spreading the fingers increases and bringing fingers closer together decreases the average of the price category.

While the embodiments illustrated in FIGS. 23 and 24 relate to cars, systems and methods described herein could be applied in other areas types of multidimensional information, for example houses where dimensions might include square footage, number of rooms, price, location, etc.

Figure 25:
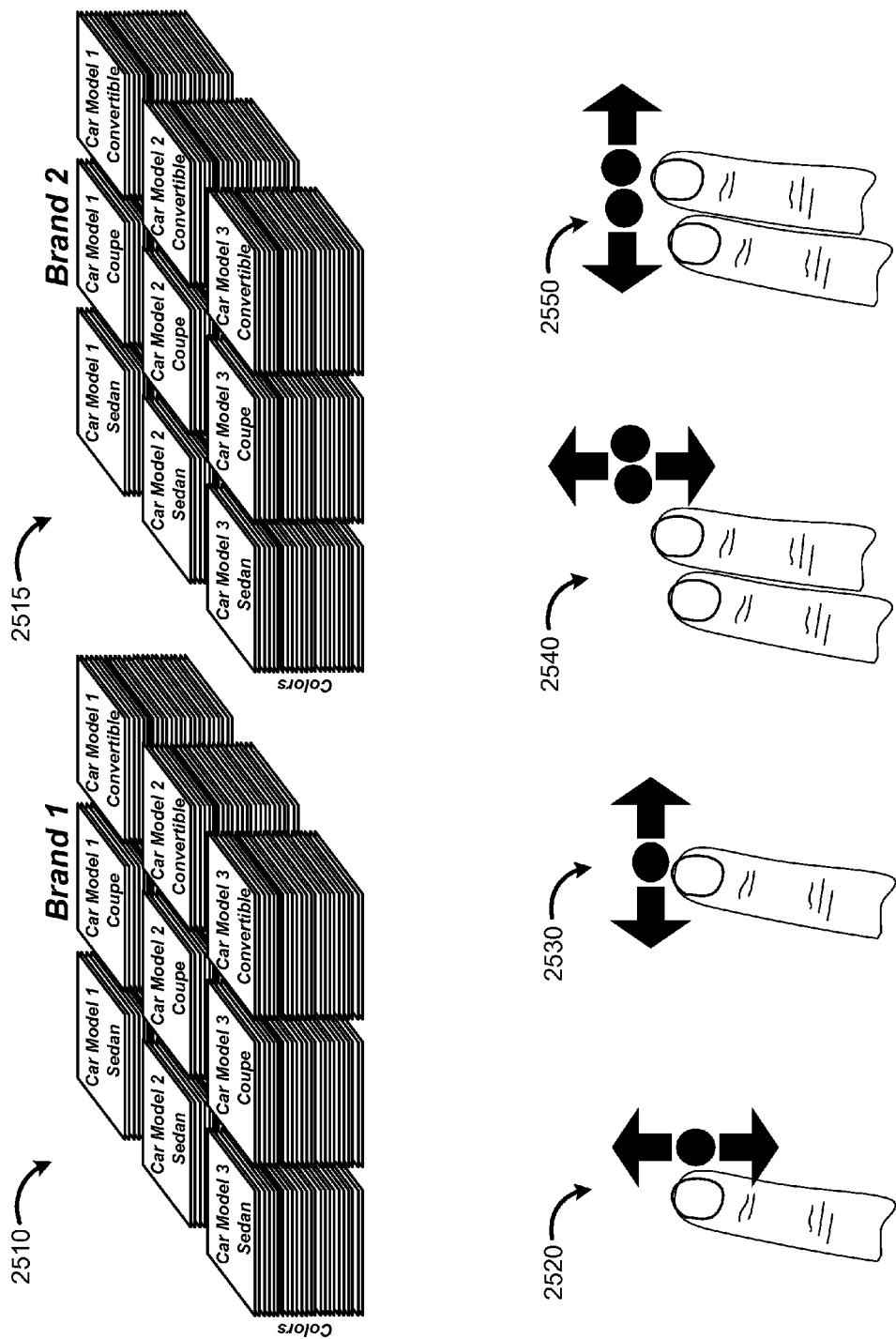
FIG. 25 illustrates stacks of information that are separated by a first criteria (e.g., brand), and that each have multiple navigable dimensions within the first criteria.

FIG. 25 illustrates stacks of information that are separated by a first criteria (e.g., brand), and that each have multiple navigable dimensions within the first criteria. For example, information 2510 is associated with Brand 1 while information 2515 is associated with Brand 2. A two finger left or right swipe shown in view 2550 could be used to navigate between brands, and then the other illustrated dimensions of model, configuration, and color may be navigated in the manner discussed above, or in any other manner.

Example user input for navigating these 4 dimensions of information are illustrated in views 2520, 2530, 2540 and 2550, where the gestures in 2520, 2530, and 2540 are as described for views 2320, 2330, and 2340 in FIG. 23.

Figure 26:
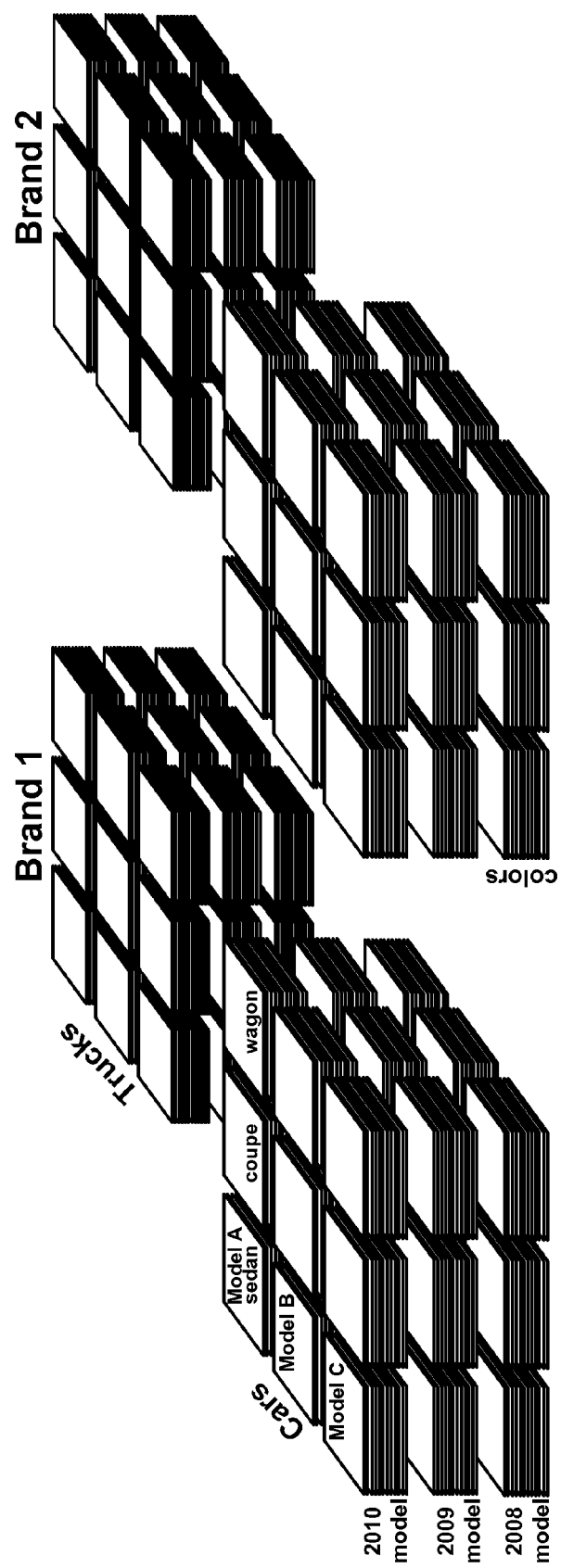
FIG. 26 illustrates the addition of another dimension to the arrangement of FIG. 25.

FIG. 26 illustrates the addition of another dimension by which information in the illustrated stacks (e.g., pictures, performance information, pricing information, dealer information, etc.) may be navigated. In particular, a dimension that allows navigation between cars and trucks has been added, where the other dimensions can be navigated as discussed above. In this embodiment, 6 different dimensions of information related to cars (e.g., Brand, Cars vs. Trucks, Model, Configuration of models, Vehicle color, Model year) may be navigated with predefined user input commands and/or customizable input commands.

Figure 27:
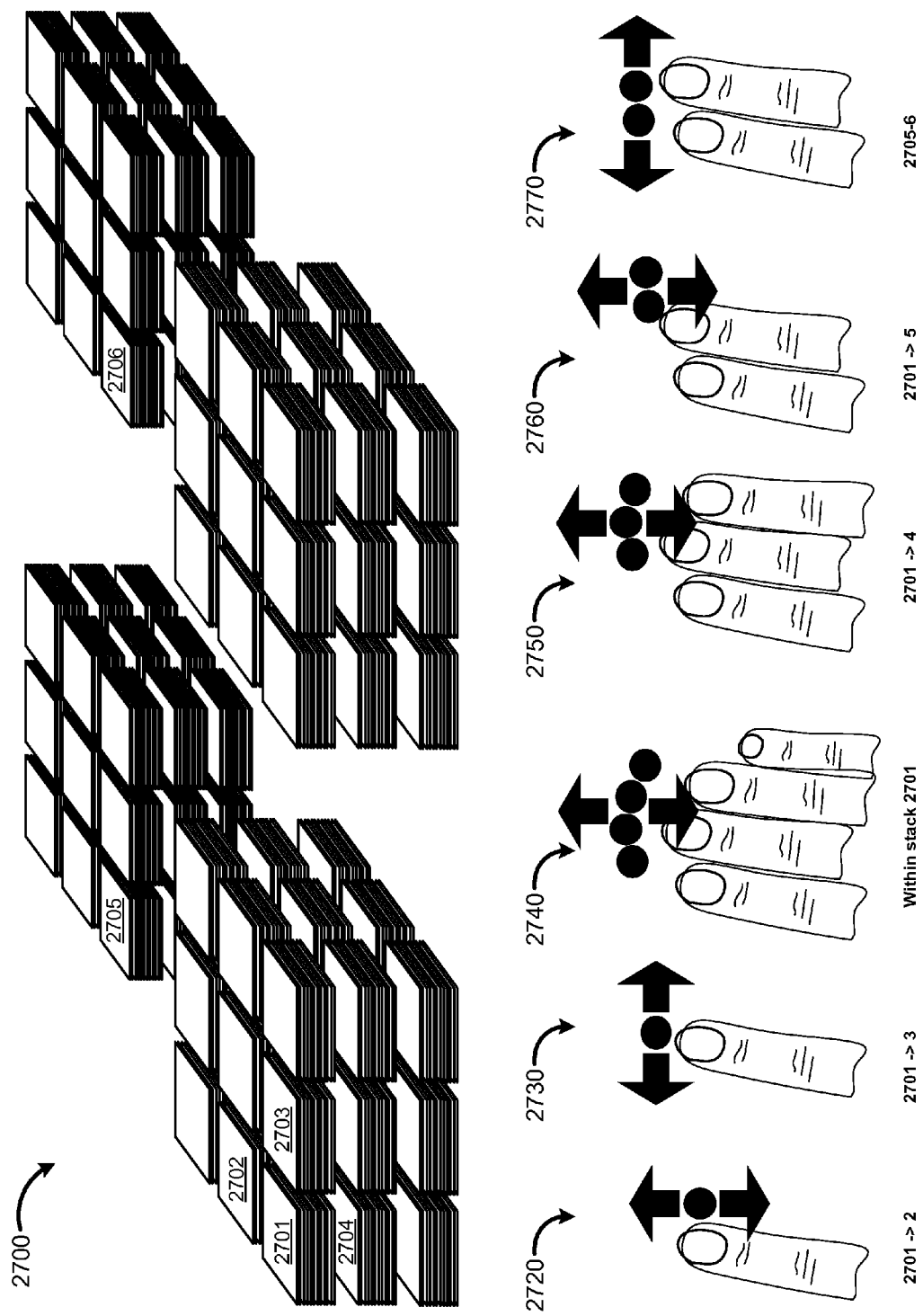
FIG. 27 illustrates a conceptual information structure with 6 dimensions of information, for example information stored in a data structure.

FIG. 27 illustrates a conceptual information structure with 6 dimensions of information, for example information stored in a data structure. In other embodiments, this information may be settings, for example to configure products. In other embodiments, the systems could be used to provide input to a computing system used to control an operation or control display of information. While 6 dimensions are shown in this embodiment, systems and methods described herein may be used with more or fewer dimensions. Systems and methods described herein may be used with categorical information, continuous information or both. For example, one dimension might be a set of colors (categorical) while another dimension may be brightness (continuous).

View 2720 illustrates an up or down movement of a single finger on the touchscreen resulting, for example, in change of position from 2701 to 2702.

In one embodiment, incremental application of a gesture results in incremental motion along a "direction".

View 2730 illustrates a left or right movement of a single finger on the touchscreen resulting, for example, in change of position from 2701 to 2703.

View 2740 illustrates an up or down movement of four fingers on the touchscreen resulting, for example, in change of position within the information stack to which item 2701 belongs.

View 2750 illustrates an up or down movement of three fingers on the touchscreen resulting, for example, in change of position from 2701 to 2704.

View 2760 illustrates an up or down movement of two fingers on the touchscreen resulting, for example, in change of position from 2701 to 2705.

View 2770 illustrates a left or right movement of two fingers on the touchscreen resulting, for example, in change of position from 2705 to 2706.

Figure 28:
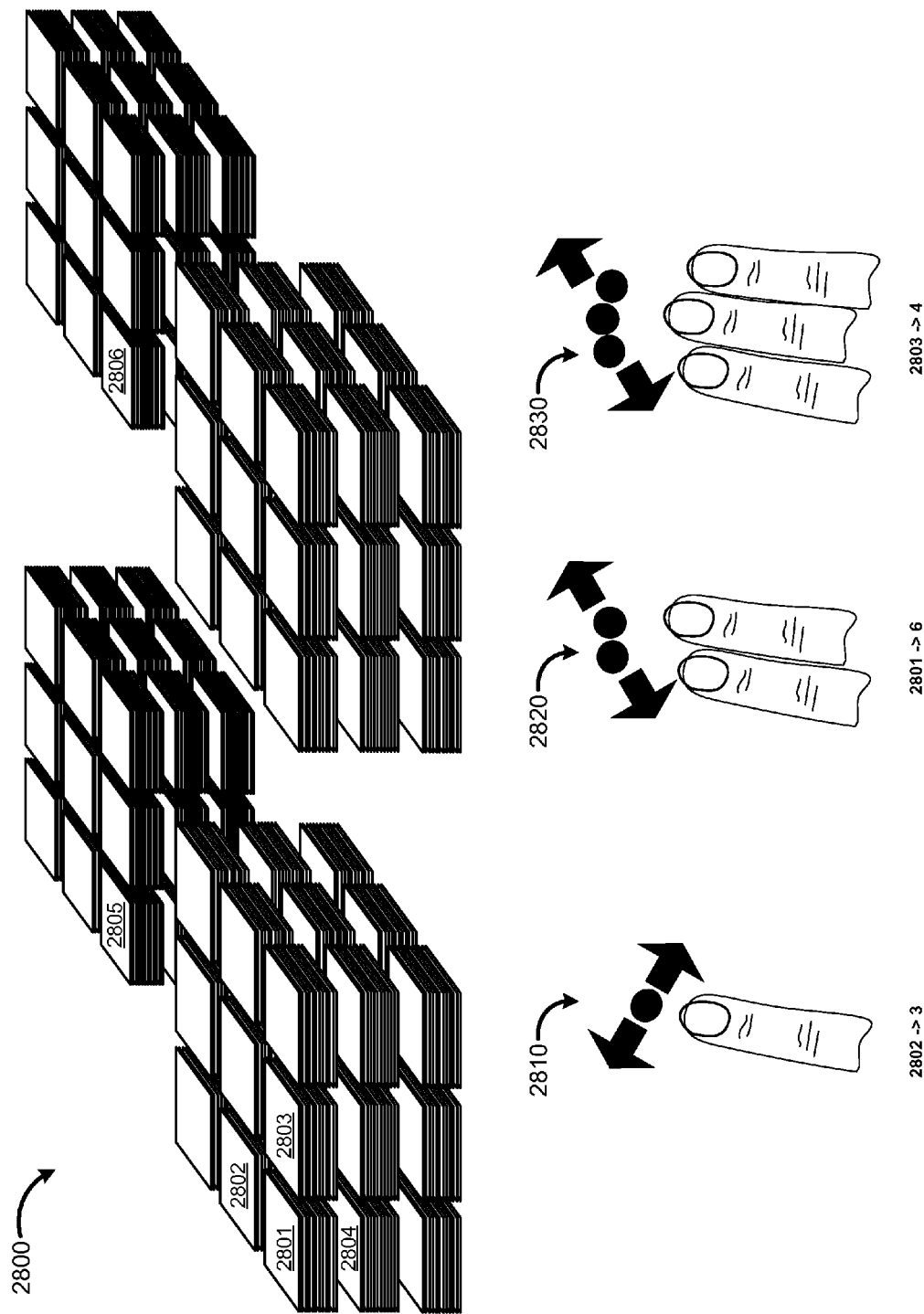
FIG. 28 illustrates example gestures that include movement in multiple dimensions.

FIG. 28 illustrates example gestures that include movement in multiple dimensions. For example, View 2810 illustrates a diagonal single finger motion, up-left or down-right, that may result, for example in movement from 2802 to 2803.

View 2820 illustrates a diagonal two finger motion, down-left or up-right, that may result, for example in movement from 2801 to 2806.

View 2830 illustrates a diagonal three finger motion, down-left or up-right, that may result, for example in movement from 2803 to 2804.

Figure 29:
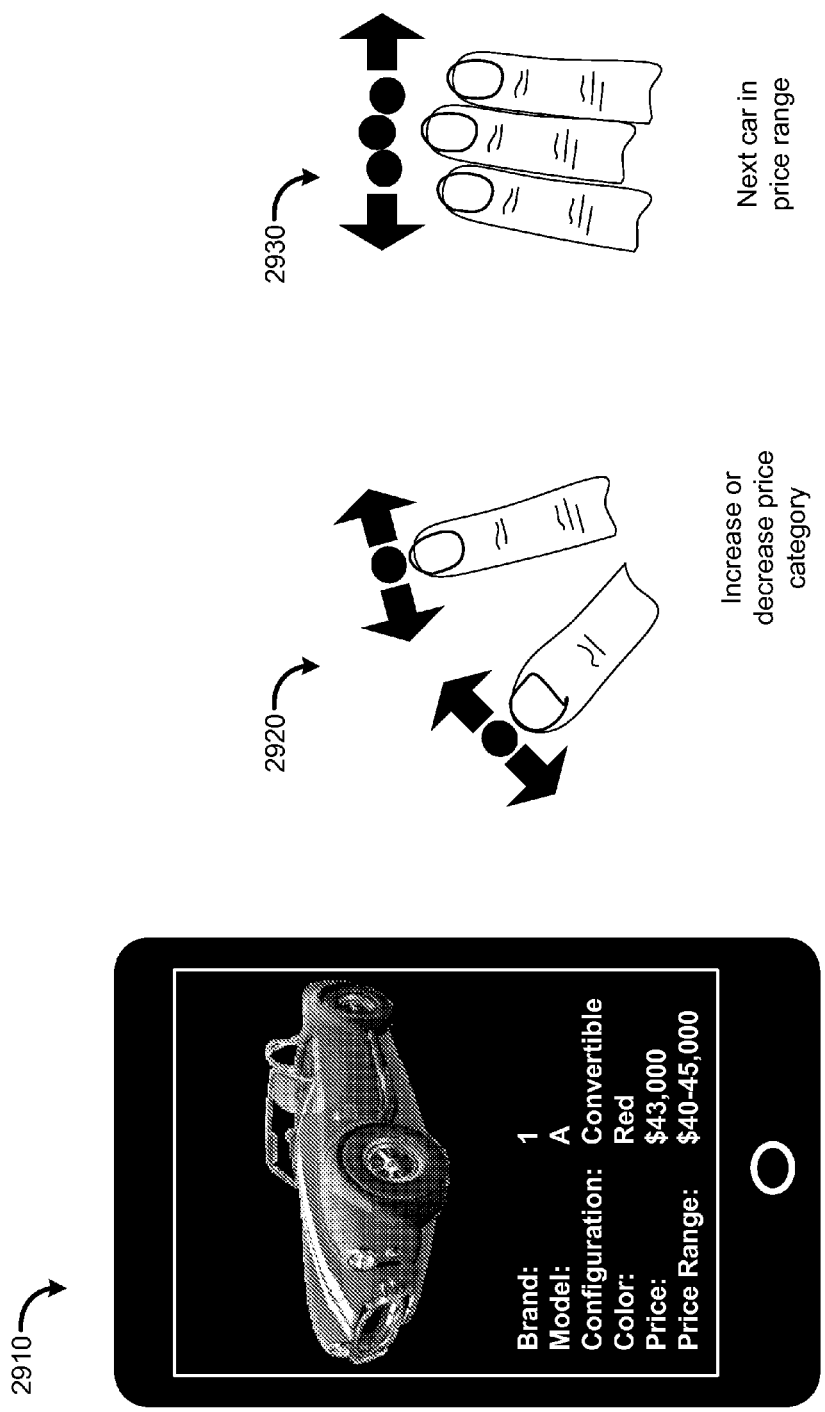
FIG. 29 illustrates a user interface wherein the user can navigate among seven dimensions of information related to an automobile.

FIG. 29 illustrates a user interface 2910 wherein the user can navigate among seven dimensions of information related to an automobile. Such navigation techniques may be used to navigate through automobiles that are available in the inventory of one or more local, regional or national dealerships, for example. While similar to the embodiment of FIG. 26, which includes 6 dimensions, views 2920 and 2930 illustrate gestures that may be used to navigate among a $7^{th}$ dimension, price in this example.

View 2920 illustrates a two-finger pinch gesture where spreading fingers apart might result in an increase in the mean value of the desired price category and moving fingers together might result in a decrease in the mean value of the desired price category.

View 2930 illustrates a gesture where moving three fingers to the right or left might result in display of the next or prior car within the price category that otherwise meets the other 6 selected dimensions.

Other

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an information display computing device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, hard disk drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of navigating between images of multiple image series, wherein each image series comprises multiple images, the method comprising:
   accessing, by a computing device having one or more computer processors, a data store storing a plurality of medical exams, at least some of the medical exams including a plurality of series of images, at least some of the series of images including a plurality of images, wherein each series of images is associated with a series type; and
   displaying, on a display of the computing device, a first image of a first series of images of a first series type within a first exam of a patient, wherein the first series of images includes a first plurality of images each depicting respective anatomic positions of an anatomic portion of the patient;
   wherein, while the first image of the first series of images is displayed, the computing device is configured to:
      in response to receiving a first input from a user of the computing device, display, on the display of the computing device, another image in the first series of images in place of the first image of the first series of images;
      in response to receiving a second input, different from the first input, from the user of the computing device:
         identify a second series of images within a second exam of the patient, the second series of images being of the first series type;
         determine an anatomic position of the first image of the first series of images within the anatomic portion of the patient;
         select a second image from the second series of images depicting the same determined anatomic position of the patient, wherein the second series of images includes a second plurality of images each depicting respective anatomic positions of the same anatomic portion of the patient; and
         display, on the display of the computing device, the second image in place of the first image of the first series of images; and
      in response to receiving a third input, different from the first and second inputs, from the user of the computing device:
         identify a third series of images within the first exam of the patient, wherein a third series type of the third series of images is different than the first series type;
         determine an anatomic position of the first image of the first series of images within the anatomic portion of the patient;
         select a third image from the third series of images depicting the same determined anatomic position of the patient, wherein the third series of images includes a third plurality of images each depicting respective anatomic positions of the same anatomic portion of the patient; and
         display the third image in place of the first image of the first series of images.

2. The method of claim 1, wherein the first input comprises movement of a single finger on a touch sensitive input device in a first direction and the second input comprises movement of two fingers on the touch sensitive input device.

3. The method of claim 2, wherein the second input comprises movement of two fingers on the touch sensitive input device in the first direction.

4. The method of claim 2, wherein the third input comprises movement of the single finger on the touch sensitive input device in a second direction that is substantially perpendicular to the first direction.

5. The method of claim 1, wherein identifying the second series of images being of the first series type comprises determining similarities between the first series of images and the second series of images.

6. The method of claim 1, wherein identifying the second series of images being of the first series type comprise determining the second series of images based on similarities between the first series type and a second series type of the second series of images.

7. The method of claim 1, wherein the second image of the second series of images within the second exam is not an initial image of the second series of images.

8. The method of claim 1, wherein the second image of the second series of images within the second exam is selected based on an image number of the second image of the second series matching an image number of the first image of the first image series.

9. The method of claim 1, wherein respective series types indicate anatomic plane, projection, orientation, or 3D volumetric display of images of respective series.

10. The method of 1, wherein the selected second image is generated using Multiplanar Reconstruction (MPR) or Maximum Intensity Projection reconstruction (MIP).

11. A computing system comprising:
   one or more computer processors,
   a touch sensitive input device configured to detect user interactions with the touch sensitive input device; and
   a tangible computer readable medium storing:
      a data structure indicating relationships between series of images of respective exams, each of the exams including a plurality of series of images, each of the series of images including a plurality of images; and
      software instructions configured for execution by the one or more computer processors,
   wherein, when executed by the one or more computer processors, the software instructions cause the computing system to perform operations comprising:
      displaying, on a display, a first image of a first series of images within a first exam of a patient, wherein the first series of images depicts respective anatomic positions of an anatomic portion of the patient;
      in response to a first user interaction:
         automatically selecting a second series of images of a second exam based on a relationship in the data structure between a first series type of the first series of images and a second series type of the second series of images, wherein the relationship indicates the first series type and the second series type are the same or similar, and wherein the second series of images depicts respective anatomic positions of the same anatomic portion of the patient;
         determining an anatomic position of the first image of the first series of images within the anatomic portion of the patient; and
         selecting a second image from the second series of images depicting the same determined anatomic position of the first image; and
         displaying the selected second image in place of the first image on the display.

12. A method of navigating between images of multiple image series, wherein each image series comprises multiple images, the method comprising:

accessing medical exam image data comprising at least a first series of images of a first series type and a second series of images of a second series type, each of the first and second series of images being related to a particular medical exam of a patient, wherein the first series of images includes a plurality of images each depicting respective anatomic positions of an anatomic portion of the patient, wherein the second series of images includes a plurality of images each depicting respective anatomic portions of the same anatomic portion of the patient;

displaying, on a display of a computing device having one or more computer processors, a first image of the first series of images;

wherein, while displaying the first image of the first series of images, the computing device is configured to:
in response to receiving a first input from a user of the computing device:
select a second image in the first series of images; and
display the selected second image on the display of the computing device in place of the first image; and
in response to receiving a second input, different from the first input, indicating a request to display images of the second series of images, from the user of the computing device:
determine an anatomic position of the first image of the first series of images within the anatomic portion of the patient;
select a second image from the second series of images depicting the same determined anatomic position of the patient; and
display the selected second image from the second series of images on the display of the computing device in place of the first image.

13. The method of claim 12, wherein the anatomic position includes one or more of an anatomic location, plane, projection, orientation, or 3D view.

14. The method of claim 12, wherein at least one of the first input and second input comprise multi-touch actions performed by the user on a touch sensitive input device.

15. The method of claim 14, wherein the touch sensitive input device comprises a touchscreen device or a touchpad.

16. The method of claim 12, wherein at least one of the first input and second input comprises actions detected based on movement of at least a portion of the user.

17. The method of claim 16, wherein the actions are detected based on images of the at least a portion of the user acquired with an image capture device.

18. The method of claim 12, wherein, further while displaying the first image of the first series of images, the computing device is configured to:
in response to receiving a third input, different from the first and second inputs, from the user of the computing device, select a third image from a third series of images of another medical exam, wherein the third series of images is automatically selected to substantially match a third series type of the third series of images with the first series type; and
display the selected third image on the display of the computing device in place of the first image.

19. The method of claim 18, wherein respective series types indicate anatomic plane, projection, orientation, or 3D volumetric display of images of respective series.

20. The method of claim 18, wherein the third input comprises movement of two fingers on the touch sensitive input device in a first direction.

21. The method of claim 12, wherein the first input comprises movement of a single finger on a touch sensitive input device in a first direction and the second input comprises movement of the single finger on the touch sensitive input device in a second direction that is substantially perpendicular to the first direction.

22. The method of claim 12, wherein the second series of images is identified based on similarities between the first series of images and the second series of images.

23. The method of claim 12, wherein the second series of images is identified based on similarities between the first series type and the second series type of the second series of images.

24. The method of claim 12, wherein the second image of the second series of images is not an initial image of the second series of images.

25. The method of claim 12, wherein the second image of the second series of images is selected based on an image number of the second image of the second series of images matching an image number of the first image within the first image series.

26. The method of claim 12, wherein the first series type is the same as the second series type of the second series of images.

27. The method of claim 12, wherein the first series type is not the same as the second series type of the second series of images.

28. The method of claim 12, wherein the first and/or second image is reconstructed from an imaging volume to substantially match the anatomic position of the first image.

29. The method of claim 28, wherein the anatomic position includes one or more of an anatomic location, plane, projection, orientation, or 3D view.

* * * * *